US011694335B2

(12) United States Patent
Mahadik et al.

(10) Patent No.: US 11,694,335 B2
(45) Date of Patent: Jul. 4, 2023

(54) SYSTEMS AND METHODS FOR DISPLAYING MEDICAL IMAGING DATA

(71) Applicant: Stryker Corporation, Kalamazoo, MI (US)

(72) Inventors: Amit Mahadik, Kalamazoo, MI (US); John Shen, Kalamazoo, MI (US); Ramanan Paramasivan, Kalamazoo, MI (US); Ben Feingold, Kalamazoo, MI (US); Robert Jones, Kalamazoo, MI (US); Brandon Hunter, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 144 days.

(21) Appl. No.: 16/703,776

(22) Filed: Dec. 4, 2019

(65) Prior Publication Data
US 2020/0184640 A1   Jun. 11, 2020

Related U.S. Application Data

(60) Provisional application No. 62/775,622, filed on Dec. 5, 2018.

(51) Int. Cl.
*G06T 7/12* (2017.01)
*A61B 1/00* (2006.01)
(Continued)

(52) U.S. Cl.
CPC .......... *G06T 7/12* (2017.01); *A61B 1/000094* (2022.02); *A61B 1/000095* (2022.02);
(Continued)

(58) Field of Classification Search
None
See application file for complete search history.

(56) References Cited

U.S. PATENT DOCUMENTS 899,478 A    9/1908 Wolf
6,824,539 B2   11/2004 Novak
(Continued)

FOREIGN PATENT DOCUMENTS

EP    2719318 A1    4/2014
WO   2017/127929 A1   8/2017

OTHER PUBLICATIONS

US 11,471,185 B2, 10/2022, Plewe (withdrawn)*
(Continued)

*Primary Examiner* — Randolph I Chu
(74) *Attorney, Agent, or Firm* — Morrison & Foerster LLP

(57) ABSTRACT

A system for displaying medical imaging data comprising one or more data inputs, one or more processors, and one or more displays, wherein the one or more data inputs are configured for receiving first image data generated by a first medical imaging device, wherein the first image data comprises a field of view (FOV) portion and a non-FOV portion, and the one or more processors are configured for identifying the non-FOV portion of the first image data and generating cropped first image data by removing at least a portion of the non-FOV portion of the first image data, and transmitting the cropped first image data for display in a first portion of the display and additional information for display in a second portion of the display.

36 Claims, 15 Drawing Sheets

(51) Int. Cl.
  *G06T 7/73* (2017.01)
  *G06T 7/13* (2017.01)
  *G06T 1/20* (2006.01)
  *G06T 5/00* (2006.01)
  *G06T 7/00* (2017.01)
  *G06T 11/00* (2006.01)

(52) U.S. Cl.
  CPC .......... *A61B 1/000096* (2022.02); *G06T 1/20* (2013.01); *G06T 5/002* (2013.01); *G06T 7/0012* (2013.01); *G06T 7/13* (2017.01); *G06T 7/73* (2017.01); *G06T 11/00* (2013.01); *G06T 2200/24* (2013.01); *G06T 2207/10016* (2013.01); *G06T 2207/20132* (2013.01); *G06T 2207/30101* (2013.01)

(56) References Cited

U.S. PATENT DOCUMENTS

| | | | |
|---|---|---|---|
| 7,492,932 | B2 | 2/2009 | Schofield |
| 7,844,657 | B2 | 11/2010 | Novak |
| 8,069,420 | B2 | 11/2011 | Plummer |
| 8,502,876 | B2 | 8/2013 | Wang et al. |
| 9,060,674 | B2 | 6/2015 | Amling |
| 9,319,483 | B2 | 4/2016 | Mussoff et al. |
| 9,687,140 | B2 | 6/2017 | Amling |
| 9,757,507 | B2 | 9/2017 | Holoien et al. |
| 10,026,159 | B2 | 7/2018 | Walle-jensen |
| 10,650,561 | B2 * | 5/2020 | Tao .............. G06T 11/60 |
| 10,748,319 | B1 * | 8/2020 | Tao .............. G06T 7/33 |
| 2009/0231418 | A1 * | 9/2009 | Higuchi .......... G06T 3/40 348/74 |
| 2010/0240953 | A1 | 9/2010 | Murakami |
| 2011/0228998 | A1 * | 9/2011 | Vaidya ........... G01R 33/543 324/309 |
| 2013/0109915 | A1 * | 5/2013 | Krupnik ......... G06F 3/04845 600/109 |
| 2013/0286255 | A1 * | 10/2013 | Suzuki ........... G03B 19/023 348/239 |
| 2016/0058277 | A1 | 3/2016 | Selcho et al. |
| 2016/0105606 | A1 * | 4/2016 | Hikita .......... H04N 5/2256 348/65 |
| 2016/0117823 | A1 * | 4/2016 | Isaacs ........... G06T 11/60 715/863 |
| 2017/0046826 | A1 * | 2/2017 | Konen .......... G06T 3/0068 |
| 2017/0165008 | A1 * | 6/2017 | Finley ......... A61B 6/5235 |
| 2017/0293134 | A1 | 10/2017 | Otterstrom et al. |
| 2018/0028079 | A1 | 2/2018 | Gurevich |
| 2018/0262696 | A1 * | 9/2018 | Amano ......... A61B 1/00195 |
| 2018/0271615 | A1 * | 9/2018 | Mahadik ........ A61B 5/0077 |
| 2018/0316943 | A1 | 11/2018 | Todd |
| 2020/0013164 | A1 * | 1/2020 | Elmaanaoui ..... G06T 7/33 |
| 2020/0160521 | A1 * | 5/2020 | Wang ........... A61B 3/0025 |
| 2020/0326784 | A1 * | 10/2020 | Isaacs .......... G06T 7/0016 |
| 2021/0153719 | A1 * | 5/2021 | Kobayashi ...... H04N 5/3572 |

OTHER PUBLICATIONS

Wang et al. "Endoscope field of view measurement" vol. 8, No. 3 | Mar. 1, 2017 | Biomedical Optics Express 1441 (Year: 2017).*

Braun et al., (2009). "Adaptive real-time image processing exploiting two dimensional reconfigurable architecture," Journal of Real-Time Image Processing 4(2): 109-125.

Eckert et al., (2016). "Operating System Concepts for Reconfigurable Computing: Review and Survey," International Journal of Reconfigurable Computing; 12 pages.

International Preliminary Report on Patentability dated Jun. 8, 2021, directed to International Application No. PCT/US2019/064478; 17 pages.

International Search Report and Written Opinion dated Apr. 16, 2020, directed to International Application No. PCT/US2019/064478; 23 pages.

Invitation to Pay Additional Fees and, where Applicable, Protest Fee and Partial International Search dated Feb. 18, 2020, directed to International Application No. PCT/US2019/064478; 19 pages.

Kruger et al., (2004). "Evaluation of Computer-assisted Image Enhancement in Minimal Invasive Endoscopic Surgery," New Image Enhancement Methods for Surgery: 362-366.

Tadigotla et al. "Dynamic Image Filter Selection using Partially Reconfigurable FPGAs for Imaging Operations," Proceedings of the 5th WSEAS Int. Conf. on Circuits, Systems, Electronics, Control & Signal Processing, Nov. 1-3, 2006, Dallas, Texas, United States of America; pp. 1-6.

* cited by examiner

SYSTEMS AND METHODS FOR DISPLAYING MEDICAL IMAGING DATA

REFERENCE TO RELATED APPLICATIONS

This application claims the benefit of U.S. Provisional Application No. 62/775,622, filed Dec. 5, 2018, the entire contents of which are hereby incorporated by reference herein.

FIELD

The present disclosure relates generally to medical imaging, and more particularly to the processing of medical imaging for visualization of tissue.

BACKGROUND

With the advent of high-definition (HD) and Ultra HD/4K resolutions in surgical visualization, the 16:9 aspect ratio surgical display has become increasingly common. However, many minimally-invasive surgical procedures still rely on an optical scope that results in a field of view at the image sensor that is smaller than the image sensor sensing area. This results in images and video having a circular field of view area within a substantial area of black pixels. In many cases, for example, the utilization is only 44% of the usable imager area, which can result in utilization of only 44% of usable display area. This is especially true for smaller diameter scopes, typically the 4 mm scopes used in arthroscopy and ENT/Neuro procedures.

When surgeons need to view multiple sources of information, such as multiple low utilization optical scope imaging, the surgeons may have to either switch the input on their primary surgical display between the various imaging feeds, use picture-in-picture or picture-by-picture mode on the surgical display, or look at two different monitors, which might be in two different locations in the operating room. All of these options can cause either a sub-optimal usage of the viewable area of the surgical display or cause the surgeon to context switch between focusing on one display to the other.

SUMMARY

According to some embodiments, medical imaging processing systems are configured to process and combine medical imaging data to generate display feeds that provide enhanced display of medical imaging. According to some embodiments, the medical imaging processing systems can combine multiple imaging data streams into one or more display streams for displaying data from multiple imaging sources and other imaging session related information sources together in a single display layout. According to some embodiments, utilization of display layouts can be optimized by removing unused portions of imaging data, such as data generated by portions of an imager that are outside of a captured field of view. In some embodiments, display feeds can be generated according to imaging session specific preferences tailored to specific types of imaging sessions and/or to specific imaging system users. In some embodiments, a reconfigurable hardware processor of the medical imaging processing system may be reconfigured from one imaging session to another to provide imaging data processing that is tailored to the next imaging session. Through one or more of these capabilities, the imaging processing systems can provide enhanced medical imaging visualization tailored to the preferences of the user.

According to some embodiments, a method of configuring a medical imaging processing system includes configuring a reconfigurable hardware processor of the medical imaging processing system into a first configuration for a first medical imaging session based on first configuration data stored in a memory, wherein the first configuration implements at least a first medical imaging processing algorithm; receiving first medical imaging data generated during the first medical imaging session; generating enhanced first medical imaging data at least in part by processing the first medical imaging data using the first medical imaging processing algorithm implemented in the first configuration; displaying the enhanced first medical imaging data for observation during the first medical imaging session; reconfiguring the reconfigurable hardware processor into a second configuration for a second medical imaging session based on second configuration data stored in the memory, wherein the second configuration implements at least a second medical imaging processing algorithm that is not implemented in the first configuration; receiving second medical imaging data generated during the second medical imaging session; generating enhanced second medical imaging data at least in part by processing the second medical imaging data using the second medical imaging processing algorithm implemented in the second configuration; and displaying the enhanced second medical imaging data for observation during the second medical imaging session on a display.

In any of these embodiments, the method may include receiving an input indicative of the second medical imaging session and, in response to receiving the input, automatically reconfiguring the reconfigurable hardware processor into the second configuration.

In any of these embodiments, the input may include a selection of a type of medical procedure.

In any of these embodiments, the input may include a selection of a user profile.

In any of these embodiments, the input may include selection of a default configuration profile.

In any of these embodiments, the default configuration profile may be based one or more connections to the medical imaging processing system from one or more external devices.

In any of these embodiments, the default configuration profile may be based on a field of view of a connected external device.

In any of these embodiments, the first configuration may be associated with a first type of medical procedure and the second configuration may be associated with a second type of medical procedure.

In any of these embodiments, the first medical imaging session may include performance of the first type of medical procedure on a patient and the second medical imaging session may include performance of the second type of medical procedure on the patient.

In any of these embodiments, the first configuration may be associated with a first user profile and the second configuration may be associated with a second user profile.

In any of these embodiments, the first medical imaging session may include imaging a patient and the second medical imaging session may include imaging the patient.

In any of these embodiments, the first configuration data and the second configuration data may be both associated with the same type of medical procedure.

In any of these embodiments, the first medical imaging session may be a first surgical session and the second medical imaging session may be a second surgical session.

In any of these embodiments, the at least one medical imaging processing algorithm implemented in the second configuration may include a smoke detection algorithm and generating the enhanced second medical imaging data may include enhancing clarity of one or more portions of one or more images associated with smoke.

In any of these embodiments, the first medical imaging processing algorithm may be configured to detect a feature of imaged tissue.

In any of these embodiments, the feature of imaged tissue may be tissue perfusion, a location of a blood vessel, an amount of blood flow, a dimension of imaged tissue, or a combination thereof.

In any of these embodiments, the enhanced second medical imaging data may include an overlay on at least a portion of the second medical imaging data.

In any of these embodiments, the reconfigurable hardware processor may be reconfigured prior to a start of imaging.

In any of these embodiments, one or more medical imaging processing algorithms may be implemented in both the first and second configurations.

In any of these embodiments, the second medical imaging data may include at least one of video frames and an image.

In any of these embodiments, the second medical imaging data may be received from an endoscopic imaging system.

In any of these embodiments, the second medical imaging data may be received from a camera control unit.

In any of these embodiments, the reconfigurable hardware processor may be an FPGA or a GPU.

In any of these embodiments, the method may include receiving the second medical imaging data from a first device, receiving data from a second medical device, and outputting a display feed to the display, the display feed comprising the enhanced second medical imaging data and at least a portion of the data from the second medical device.

In any of these embodiments, the method may include receiving the second medical imaging data and the data from the second medical device at a first processor, transmitting the second medical imaging data from the first processor to the reconfigurable hardware processor, receiving the enhanced second medical imaging data from the reconfigurable hardware processor at the first processor, and generating, by the first processor, the display feed by combining the enhanced second medical imaging data with the at least a portion of the data associated with the second medical device.

In any of these embodiments, the first configuration data may be stored in a remote memory and received via a network connection.

According to some embodiments, a method for displaying medical imaging data includes receiving first image data generated by a first medical imaging device, wherein the first image data comprises a field of view (FOV) portion and a non-FOV portion; identifying the non-FOV portion of the first image data; generating cropped first image data by removing at least a portion of the non-FOV portion of the first image data; and displaying the cropped first image data in a first portion of a display and additional information in a second portion of the display.

In any of these embodiments, the non-FOV portion may be identified using edge detection.

In any of these embodiments, the first image data may include a series of video frames and the edge detection may be performed on more than one frame.

In any of these embodiments, the non-FOV portion may be identified using one or more of a location of a center of the FOV portion and a measurement associated with a dimension of the FOV portion.

In any of these embodiments, the location of a center of the FOV portion and the measurement associated with a dimension of the FOV portion may be determined during an imaging session initialization process.

In any of these embodiments, the imaging session initialization process may be a white balancing process.

In any of these embodiments, the first image data may include a rectangular image or video frame and the FOV portion may be a circular portion of the rectangular image or video frame.

In any of these embodiments, the first image data may include a video frame.

In any of these embodiments, the first image data may be received on a first input of a medical imaging processing system and the additional information may be based on data received on a second input of the medical imaging processing system.

In any of these embodiments, the method may include transmitting a display feed from the medical imaging processing system to the display, the display feed comprising a combination of the cropped first image data and the additional information.

In any of these embodiments, the method may include receiving second image data generated by a second medical imaging device; identifying a non-FOV portion of the second image data; generating cropped second image data by removing at least a portion of the non-FOV portion of the second image data; and displaying the cropped second image data in the second portion of the display.

In any of these embodiments, the first image data may be received on a first input of a medical imaging processing system and the second image data may be received on a second input of the medical imaging processing system.

In any of these embodiments, the method may include transmitting a display feed from the medical imaging processing system to the display, the display feed including a combination of the cropped first image data and the cropped second image data.

In any of these embodiments, the cropped first image data and the additional information may be located on the display based on configuration data stored in a memory.

In any of these embodiments, the configuration data may include user-specified configuration data.

In any of these embodiments, the configuration data may be received via a network connection.

In any of these embodiments, the first image data may be received from an endoscopic imaging system, an intraoperative C-arm imaging system, or an ultrasound system.

In any of these embodiments, the first image data may be received from a camera control unit.

In any of these embodiments, the additional information may include one or more of patient data, metrics, a graph, an image, device status, and a video feed.

According to some embodiments, a reconfigurable medical imaging processing system includes a display; memory; a reconfigurable hardware processor; and a second processor configured for: configuring the reconfigurable hardware processor into a first configuration for a first medical imaging session based on first configuration data stored in the memory, wherein the reconfigurable hardware processor in the first configuration is configured to implement at least a first medical imaging processing algorithm and to generate enhanced first medical imaging data for display on the display at least in part by processing first medical imaging data using the first medical imaging processing algorithm, and reconfiguring the reconfigurable hardware processor into a second configuration for a second medical imaging session based on second configuration data stored in the memory, wherein the reconfigurable hardware processor in the second configuration is configured to implement at least a second medical imaging processing algorithm and to generate enhanced second medical imaging data for display on the display at least in part by processing second medical imaging data using the second medical imaging processing algorithm.

In any of these embodiments, the second processor may be configured to receive an input indicative of the second medical imaging session and, in response to receiving the input, automatically reconfigure the reconfigurable hardware processor into the second configuration.

In any of these embodiments, the input may include a selection of a type of medical procedure.

In any of these embodiments, the input may include a selection of a user profile.

In any of these embodiments, the input may include selection of a default configuration profile.

In any of these embodiments, the default configuration profile may be based on one or more connections to the medical imaging processing system from one or more external devices.

In any of these embodiments, the default configuration profile may be based on a field of view of a connected external device.

In any of these embodiments, the first configuration may be associated with a first type of medical procedure and the second configuration may be associated with a second type of medical procedure.

In any of these embodiments, the first medical imaging session may include performance of the first type of medical procedure on a patient and the second medical imaging session may include performance of the second type of medical procedure on the patient.

In any of these embodiments, the first configuration may be associated with a first user profile and the second configuration may be associated with a second user profile.

In any of these embodiments, the first medical imaging session may include imaging a patient and the second medical imaging session may include imaging the patient.

In any of these embodiments, the first configuration data and the second configuration data may be both associated with the same type of medical procedure.

In any of these embodiments, the first medical imaging session may be a first surgical session and the second medical imaging session may be a second surgical session.

In any of these embodiments, the at least one medical imaging processing algorithm implemented in the second configuration may include a smoke detection algorithm and generating the enhanced second medical imaging data may include enhancing clarity of one or more portions of one or more images associated with smoke.

In any of these embodiments, the first medical imaging processing algorithm may be configured to detect a feature of imaged tissue.

In any of these embodiments, the feature of imaged tissue may be tissue perfusion, a location of a blood vessel, an amount of blood flow, a dimension of imaged tissue, or a combination thereof.

In any of these embodiments, the enhanced second medical imaging data may include an overlay on at least a portion of the second medical imaging data.

In any of these embodiments, the system may be configured to reconfigure the reconfigurable hardware processor prior to a start of imaging.

In any of these embodiments, one or more medical imaging processing algorithms may be implemented in both the first and second configurations.

In any of these embodiments, the second medical imaging data may include at least one of video frames and an image.

In any of these embodiments, the system may be configured to receive the second medical imaging data from an endoscopic imaging system.

In any of these embodiments, the system may be configured to receive the second medical imaging data from a camera control unit.

In any of these embodiments, the reconfigurable hardware processor may be an FPGA or a GPU.

In any of these embodiments, the system may be configured to receive the second medical imaging data from a first device, receive data from a second medical device, and display the enhanced second medical imaging data and at least a portion of the data from the second medical device.

In any of these embodiments, the system may be configured to receive the second medical imaging data and the data from the second medical device at the second processor, transmit the second medical imaging data from the second processor to the reconfigurable hardware processor, receive the enhanced second medical imaging data from the reconfigurable hardware processor at the second processor, and generate, by the second processor, a display feed for the display by combining the enhanced second medical imaging data with the at least a portion of the data associated with the second medical device.

In any of these embodiments, the first configuration data may be stored in a remote memory and received via a network connection.

According to some embodiments, a system for displaying medical imaging data includes one or more data inputs; one or more processors; and one or more displays, wherein the one or more data inputs are configured for receiving first image data generated by a first medical imaging device, wherein the first image data comprises a field of view (FOV) portion and a non-FOV portion, and the one or more processors are configured for identifying the non-FOV portion of the first image data and generating cropped first image data by removing at least a portion of the non-FOV portion of the first image data, and transmitting the cropped first image data for display in a first portion of the display and additional information for display in a second portion of the one or more displays.

In any of these embodiments, the one or more processors may be configured for identifying the non-FOV portion using edge detection.

In any of these embodiments, the first image data may include a series of video frames and the one or more processors may be configured for identifying the non-FOV portion using edge detection performed on more than one frame.

In any of these embodiments, the one or more processors may be configured for identifying the non-FOV portion using one or more of a location of a center of the FOV portion and a measurement associated with a dimension of the FOV portion.

In any of these embodiments, the one or more processors may be configured for determining the location of a center of the FOV portion and the measurement associated with a dimension of the FOV portion during an imaging session initialization process.

In any of these embodiments, the imaging session initialization process may be a white balancing process.

In any of these embodiments, the first image data may include a rectangular image or video frame and the FOV portion may be a circular portion of the rectangular image or video frame.

In any of these embodiments, the first image data may include a video frame.

In any of these embodiments, the one or more data inputs may be configured for receiving the first image data on a first input of a medical imaging processing system and the additional medical imaging data may be based on data received on a second input of the medical imaging processing system.

In any of these embodiments, the medical imaging processing system may be configured for transmitting a display feed from the medical imaging processing system to the display, the display feed may include a combination of the cropped first image data and the additional medical imaging data.

In any of these embodiments, the one or more data inputs may be configured for receiving second image data generated by a second medical imaging device; and the one or more processors may be configured for: identifying a non-FOV portion of the second image data, generating cropped second image data by removing at least a portion of the non-FOV portion of the second image data, and transmitting the cropped second image data for display in a second portion of the one or more displays.

In any of these embodiments, the one or more data inputs may be configured for receiving the first image data on a first input of a medical imaging processing system and receiving the second image data on a second input of the medical imaging processing system.

In any of these embodiments, the medical imaging processing system may be configured for transmitting a display feed from the medical imaging processing system to the display, the display feed comprising a combination of the cropped first image data and the cropped second image data.

In any of these embodiments, the cropped first image data and the additional medical imaging data may be located on the display based on configuration data stored in a memory.

In any of these embodiments, the configuration data may include user-specified configuration data.

In any of these embodiments, the system is configured for receiving the configuration data via a network connection.

In any of these embodiments, the one or more data inputs may be configured for receiving the first image data from an endoscopic imaging system, an intraoperative C-arm imaging system, or an ultrasound system.

In any of these embodiments, the one or more data inputs may be configured for receiving the first image data from a camera control unit.

In any of these embodiments, the additional information may include one or more of patient data, metrics, a graph, an image, device status, and a video feed.

According to some embodiments, a non-transitory tangible computer-readable medium includes computer-executable program code embedded thereon to perform the any of the methods above.

According to some embodiments, a kit for processing a time series of fluorescence images of tissue of a subject includes any of the systems above and/or any of the non-transitory tangible computer-readable medium above, and a fluorescence imaging agent.

According to some embodiments, a fluorescence imaging agent is provided for use in any of the methods above, in the any of the systems above, or in any of the kits above for imaging an object.

In any of these embodiments, imaging an object may include imaging an object during blood flow imaging, tissue perfusion imaging, lymphatic imaging, or a combination thereof.

In any of these embodiments, blood flow imaging, tissue perfusion imaging, and/or lymphatic imaging may include blood flow imaging, tissue perfusion imaging, and/or lymphatic imaging during an invasive surgical procedure, a minimally invasive surgical procedure, or during a non-invasive surgical procedure.

In any of these embodiments, the invasive surgical procedure may include a cardiac-related surgical procedure or a reconstructive surgical procedure.

In any of these embodiments, the cardiac-related surgical procedure may include a cardiac coronary artery bypass graft (CABG) procedure.

In any of these embodiments, the CABG procedure may be on pump or off pump.

In any of these embodiments, the non-invasive surgical procedure may include a wound care procedure.

In any of these embodiments, the lymphatic imaging may include identification of a lymph node, lymph node drainage, lymphatic mapping, or a combination thereof.

In any of these embodiments, the lymphatic imaging may relate to the female reproductive system.

Some embodiments include use of any of the methods above in any of the systems above or in any of the kits above for imaging an object for lymphatic imaging.

Some embodiments include use of any of the methods above, in any of the systems above, or in any of the kits above for imaging an object for blood flow imaging, tissue perfusion imaging, or a combination thereof.

It will be appreciated that any variations disclosed herein in connection with the methods, systems, kits and other aspects of the disclosure may be may be combined.

BRIEF DESCRIPTION OF THE DRAWINGS

The invention will now be described, by way of example only, with reference to the accompanying drawings, in which.

DETAILED DESCRIPTION

Figure 1:
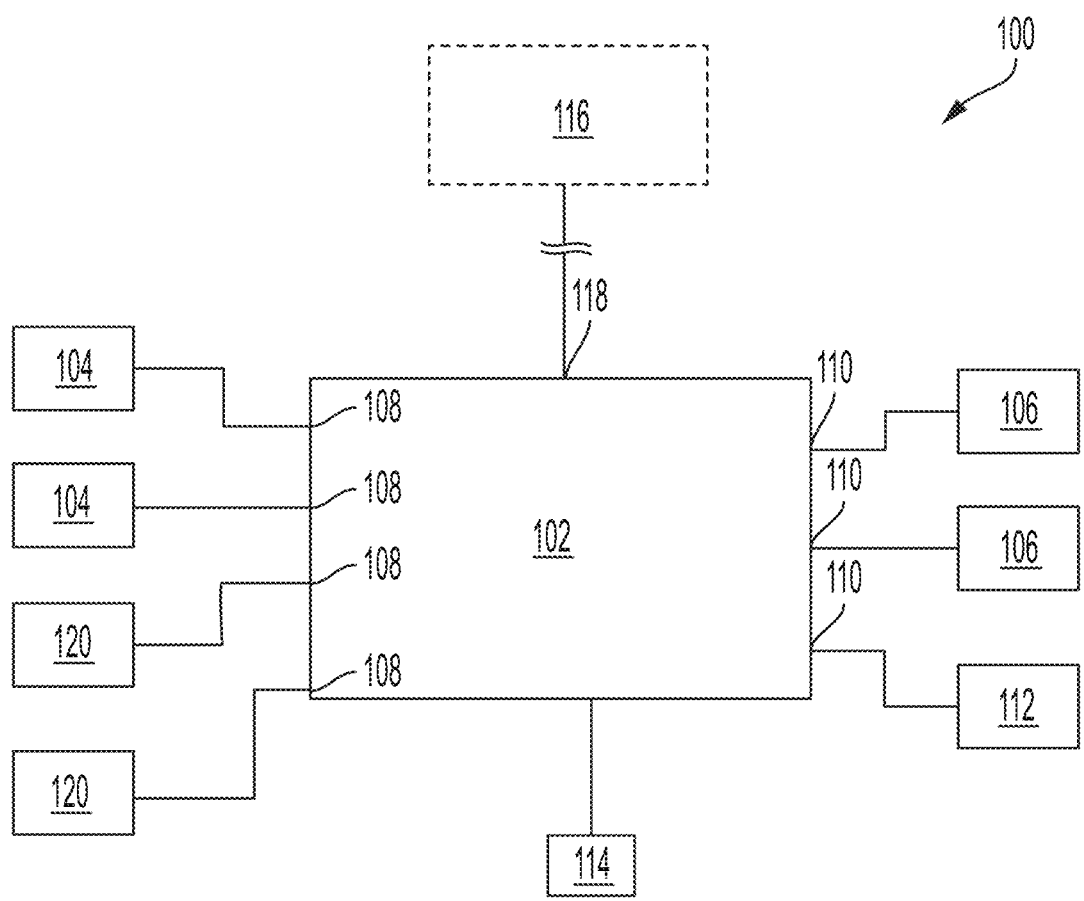
FIG. 1 is a block diagram of a system for generating and displaying medical imaging data during medical imaging sessions, according to some embodiments.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described. Described herein are systems and methods for generating enhanced medical imaging for display in connection with (e.g., during) a medical imaging session. Systems and methods can process data from multiple imaging systems to generate enhanced imaging and can stitch together multiple imaging data sets into single display feeds for displaying information from multiple sources on a single display. Imaging data can be processed to maximize utilization of displays to enable the presentation of more relevant information to the practitioner during the imaging session.

According to some embodiments, the systems and methods can process and combine imaging data differently based on the needs of each imaging session. Practitioners may be able to define the information that is displayed during their imaging sessions, ensuring that data is presented in a manner suited to the practitioner, which can reduce the amount of time needed for the practitioner to adjust data display.

In some embodiments, one or more reconfigurable hardware processors are reconfigured for each imaging session to provide imaging processing that is tailored to each imaging session. Reconfigurable hardware processors, such as field-programmable gate arrays (FPGA's) provide the low latency and high bandwidth required for real time video processing and also provide for the ability to implement different algorithms or different combinations of algorithms on different data inputs or combinations of data inputs as required from imaging session to imaging session, providing for imaging processing that is tailored to meet the differing needs of different imaging sessions. This configurability and flexibility in the ability to process and combine different input data enables a single imaging processing system, according to embodiments described herein, to support a wide variety of imaging sessions, including a wide variety of surgical procedures.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates a system 100 for generating and displaying medical imaging data during medical imaging sessions. System 100 includes a medical data processing hub 102 that processes data received from one or more imaging modalities 104 to generate one or more display feeds for displaying enhanced medical imaging on one or more displays 106. The one or more imaging modalities 104 may generate image data associated with treatment of a patient. The image data can be images or videos generated during treatment of the patient in support of one or more medical procedures, such as video captured by an endoscopic camera during an endoscopic procedure on a patient. Examples of medical imaging modalities include, without limitation, endoscopic systems, open field imaging systems, x-ray systems such as intraoperative c-arm systems, computer tomography systems, ultrasound systems, magnetic resonance imaging systems, and nuclear medicine systems.

In some embodiments, hub 102 may receive data from one or more non-imaging devices 120 that may be used in connection with (e.g., during) a medical imaging session and that may provide information that may be relevant for display during a medical imaging session. Non-limiting examples of non-imaging devices include insufflators, illumination controllers, and voice control systems.

Hub 102 may receive image data from the one or more imaging modalities 104 through one or more input ports 108. The hub 102 generates one or more display feeds using received imaging data and transmits the one or more display feeds to one or more displays 106 via one or more output ports 110. For example, the hub 102 may generate a display feed that includes enhanced imaging of tissue of a patient based on imaging generated by one or more imaging modalities 104 and the enhanced imaging may be displayed on one or more of the displays 106 to assist a practitioner during treatment of the patient. Hub 102 may also transmit display feeds to one or more recording devices 112 for recording enhanced imaging for later retrieval. Input ports 108 and output ports 110 may be any suitable types of data transmission ports, such as DVI ports, HDMI ports, RS232 ports, IP ports, and the like.

Hub 102 may be connected to one or more networks 116 via one or more network connections 118. The one or more networks may be local network such as a hospital information system or may be a wider network such as a wide area network or the internet. A network connection 118 can be a wired connection, such as an Ethernet connection, or a wireless network connection, such as a Wi-Fi connection. In some embodiments, the hub 102 may access the one or more networks 116 to retrieve configuration data stored at a network location for configuring the hub for an imaging session, and/or may access the one or more networks to receive updated software and/or updated hardware files for processing imaging data.

One or more user interfaces 114 may be connected to hub 102 for a user to provide input to the hub 102. The user may input data related for configuring the hub 102 for an imaging session. User input can include, for example, selection of a practitioner profile associated with an upcoming imaging session, selection of a type of imaging session or types of procedure to be performed during an imaging session, or any other relevant information. The one or more user interfaces 114 may include a tablet, a keyboard, a mouse, a voice control system, a keypad, a touchscreen, or any combination thereof.

As described in detail below, the hub 102 processes received medical imaging data and any other relevant data and generates enhanced display feeds for display on one or more displays 106 during an imaging session. According to some embodiments, the hub 102 can combine multiple imaging sources into a single display feed, can process received imaging data to generate richer imaging data, can modify imaging data for better utilization of display space, and/or can reconfigure the processing of imaging data depending on the needs and preferences of users from imaging session to imaging session.

Figure 2:
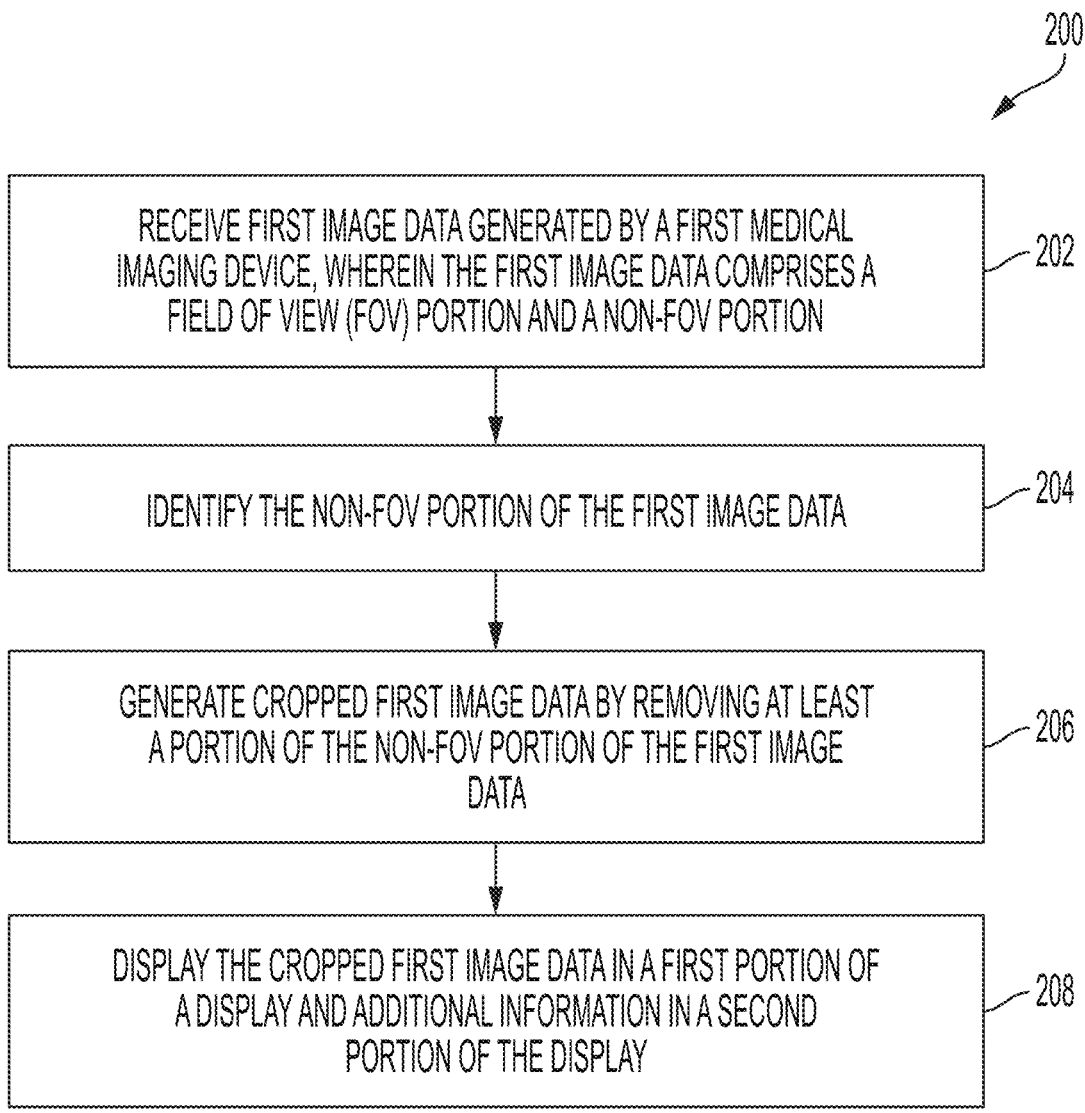
FIG. 2 illustrates a method for displaying medical imaging data, according to some embodiments.

FIG. 2 illustrates a method 200 for displaying medical imaging data, according to some embodiments. Method 200 may be performed by a medical imaging data processing hub, such as medical imaging data processing hub 102 of system 100. Method 200 is performed for removing unutilized portions of received imaging data to better utilize display space, which can provide the ability to display more relevant information to users during an imaging session.

In many conventional imaging systems such as scope-based imaging systems, including for example endoscopic imaging systems, a generally circular area light from the scene is projected on the light-sensitive portions of the imaging sensor or sensors. This is due to the sensor or sensors of the imager being generally larger in area than the area of light provided by the scope optics. Therefore, the imaging captured by the sensor or sensors includes a field of view (FOV) portion representing the light received from the field of view and a non-FOV portion generated by portions (i.e., pixels) of the sensor or sensors that do not receive light from the scene, often resulting in a rectangular image having a circular FOV portion in the middle that shows the imaged scene surrounded by black non-FOV portions (or near black due to sensor noise). When the endoscopic imaging is displayed in a conventional manner, a large portion of the display is taken up by the non-FOV portion, which displays black pixels that do not provide any useful information.

Figure 3A:
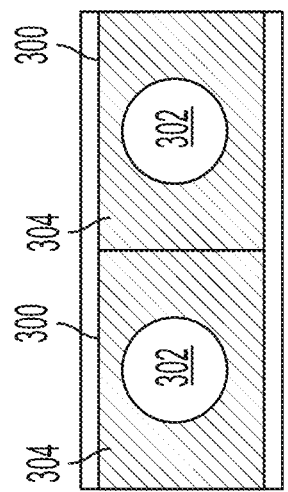
FIG. 3A illustrates an exemplary image generated by an endoscopic imager and FIG. 3B illustrates two endoscopic images displayed side-by-side on an exemplary display.

To illustrate this concept, an imaging system such as an exemplary endoscopic image 300 is shown in FIG. 3A. Image 300 includes a FOV portion 302 generated by portions of the sensor receiving light from the imaged scene and a non-FOV portion 304 generated by portions of the sensor that do not receive light from the scene. FIG. 2B illustrates two images 300 displayed side-by-side on an exemplary display 350. As illustrated, a relatively large amount of display space is wasted due to the non-FOV portions of the two images. In some embodiments, the hub 102 can crop some or all of the non-FOV portion of received image data.

Returning to FIG. 2, at step 202, first image data that has been generated by a first medical imaging device is received by the medical imaging data processing hub. The first image data, which can be an image or video frames, includes an FOV portion and a non-FOV portion. For example, the first image data may be a video frame generated by an endoscopic camera, such as image 300 of FIG. 3A. The frame may include an FOV portion generated by pixels of the camera sensor or sensors that receive light from an imaged scene incident on the sensor or sensors and may include a non-FOV portion generated by pixels of the camera sensor or sensors that do not receive light from the imaged scene.

At step 204, the non-FOV portion of the first image data is identified. According to some embodiments, the non-FOV portion may be identified based on one or more predetermined parameters associated with the FOV portion. Examples of predetermined parameters include a center of the FOV portion, a radius or diameter of the FOV portion, and pixel locations associated with the FOV portion or non-FOV portions. Pixels that are outside of an area defined by the predetermined parameters may be identified as the non-FOV portion.

In some embodiments, parameters associated with an FOV portion of data received from a connected device may be determined once and used repeatedly as new image data is received from the device to identify the non-FOV portions of the data received from the connected device. For example, a center and diameter (or radius) of a FOV portion may be determined based on image data received from a connected device and this center and diameter (or radius) may be used to identify the non-FOV portion in future image data received from the device. In some embodiments, one or more edge detection algorithms are used to detect the edge of the FOV portion and the edge data may be used to identify non-FOV portions of an image or may be used to determine the center and diameter (or radius) of the FOV portion, which in turn, is used to identify non-FOV portions of an image.

In some embodiments, one or more parameters associated with a FOV portion of image data received from a connected device are determined during an imaging session initialization phase of the connected device in which images are captured that have a sharp boundary between the FOV portion and the non-FOV portion. This initialization phase may be, for example, a white balance phase in which an imager is directed toward a white surface to allow for the imager and/or associated light source to adjust one or more imaging parameters such as gain and light intensity based on an amount of light received from the white surface. During the white balance phase, the FOV portion of image data generated by the imager, which is directed at a white background, is relatively bright and, as such, has high contrast with the non-FOV portion, which is black, providing a clear edge that can be readily detected using one or more edge detection algorithms.

In some embodiments, the medical imaging data processing hub receives an indication from a connected device that the connected device is in an initialization phase, such as a white balance phase. In response to receiving this indication, the medical imaging data processing hub performs an edge detection process to determine the location of the FOV portion of the image data received from the connected device. The determined location of the FOV portion (e.g., center, diameter, pixel locations, etc.) can be used to identify the non-FOV portion of image data subsequently received.

In some embodiments, the non-FOV portion may be identified by detecting the location of the perimeter of the FOV portion for each received image or frame. In some embodiments, the perimeter of the FOV portion in the first image data may be detected using, for example, one or more edge detection algorithms.

At step 206, cropped first image data is generated by removing at least a portion of the non-FOV portion of the first image data. The non-FOV portion or portions that are removed may be selected based on any suitable cropping criteria, including a desired aspect ratio for a cropped image or a predefined size of a cropped image. For example, a cropping criteria may specify that the cropped image should be square and, based on this criteria, non-FOV portions that are outside of a square encompassing the FOV portion may be removed, resulting in a square cropped image. Alternatively, a cropping criteria may specify an aspect ratio and, based on this criteria, non-FOV portions of a rectangle encompassing the FOV portion may be removed, resulting in a cropped image having the specified aspect ratio.

In some embodiments, one or more cropping criteria used in step 206 may be based on one or more properties of a connected display. For example, the dimensions of the display may be used to determine the bounds of the cropped image. The display dimensions may be divided into display sections and the dimensions of the display sections may determine the bounds of a cropped image. For example, in the exemplary display of FIG. 2D, the first display section 220 may be sized such that the image for display in section 220 may be cropped to the width of the FOV portion of the image for display in section 220, whereas an image for display in the second section 222 may be cropped to the height of the FOV portion of the image for display in section 222.

In some embodiments, the medical imaging data processing hub may receive information regarding the display area (i.e., pixel dimensions, spatial dimensions, etc.) from the connected display. In other embodiments, one or more display area parameters are user defined.

At step 208, a display feed is generated based on the cropped first image data. The display feed is transmitted to one or more connected displays such as display 106 of system 100, via one or more display connections, and the cropped first image data is displayed on a display. In some embodiments, the cropped first image may be displayed in a first portion of the display and additional information may be displayed in a second portion of the display. Examples of additional information that may be displayed include one or more images, videos, patient data and/or patient metadata, connected device status, metrics associated with imaging or any other connected device related information, one or more graphs, etc. According to some embodiments, by cropping the first image data, the first portion of the display may occupy less room on the display, increasing an amount of display space available for displaying the additional information. According to some embodiments, the cropped image data may be shown in a portion of the screen having a same height and/or width as would have a portion showing uncropped image data, but cropping of the image data allows for the FOV portion to be larger on the display.

In some embodiments, image data may be received from a plurality of connected devices and the image data from each connected device may be cropped according to method 200 discussed above. A display feed may be generated for displaying the multiple cropped images on one or more connected displays. In some embodiments, additional information may be displayed along with one or more cropped images. The additional information may be based on data received from one or more connected devices. For example, an insufflator system connected to the medical imaging data processing hub may transmit an insufflation pressure reading to the system and the pressure reading may be combined with a cropped endoscopic image in the display feed for displaying alongside the cropped endoscopic image on the display.

Figure 3B:
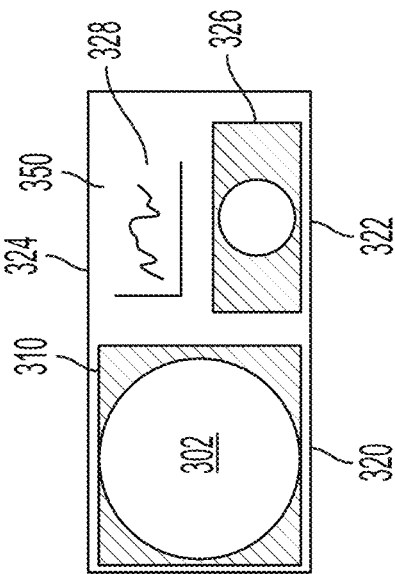
Figure 3C:
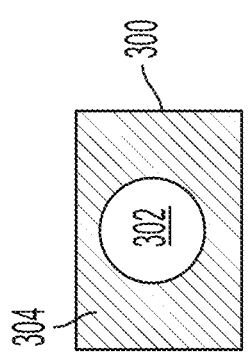
FIG. 3C illustrates an exemplary display, according to some embodiments, displaying cropped endoscopic images, according to some embodiments.
Figure 3D:
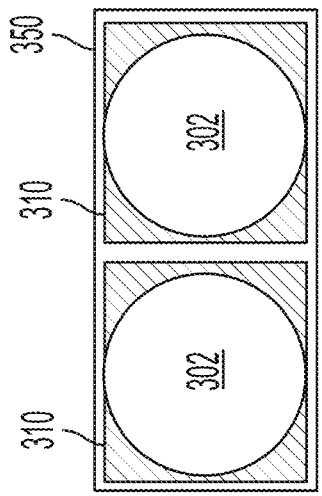
FIG. 3D illustrates an exemplary display, according to some embodiments, displaying cropped endoscopic images and additional imaging session related data, according to some embodiments.

FIG. 3C illustrates the exemplary display 350 of FIG. 3B with two cropped images 310 generated according to method 200. The cropped images 310 include the FOV portions 302 of the images 300 of FIG. 3B with portions of the non-FOV portions removed. As illustrated, cropping of the images allows for the images to be displayed much larger. Cropping of images can also provide space for additional information to be displayed. For example, in FIG. 3C, the cropped image 310 occupies a first portion 320 of the display 350, a second cropped image 326 occupies a second portion 322 of the display 350, and an exemplary graph 328 occupies a third portion 324 of the display screen. Thus, a medical imaging processing system, such as hub 102, is able to maximize utilization of a display screen for displaying medical imaging data and other information.

Figure 4:
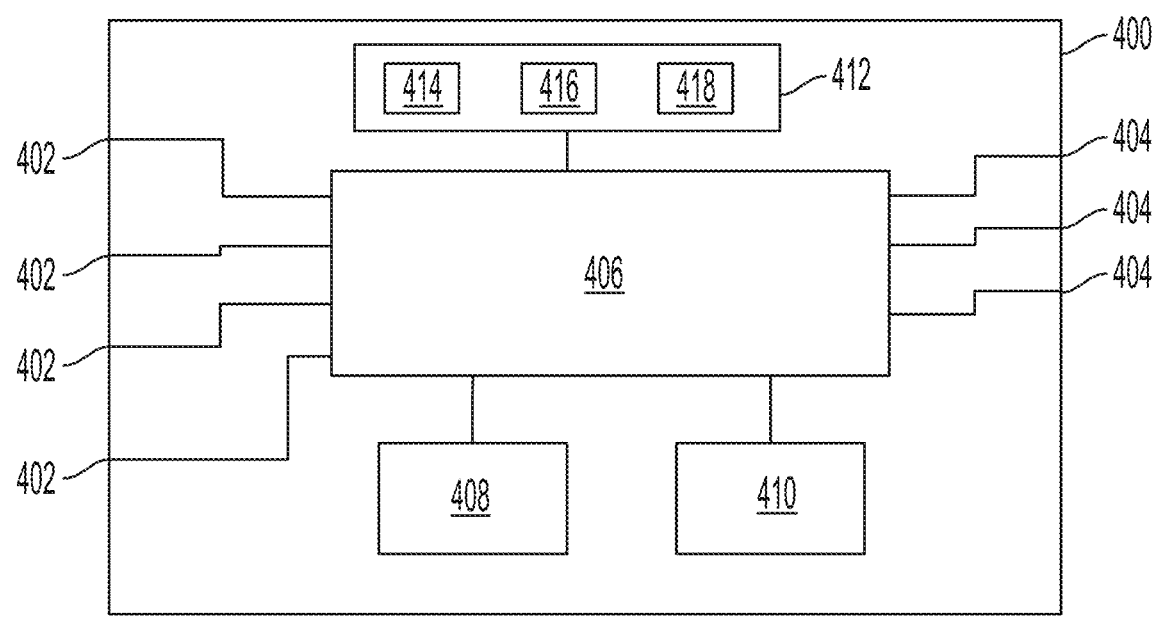
FIG. 4 is a block diagram of a medical imaging data processing hub, according to some embodiments.

FIG. 4 is a block diagram of a medical imaging data processing hub 400, according to one embodiment, that may be used in a medical imaging system, such as system 100 of FIG. 1, to process multiple data streams from connected medical devices, such as imaging devices, and generate an optimized display layout for displaying useful information to a user, such as a surgeon, during a medical procedure. Hub 400 includes one or more input connections 402 for receiving data from connected devices. Hub 400 includes one or more outputs 404 for connection to one or more display devices. Hub 400 includes a primary processing unit 406 that processes at least a portion of the data received from connected devices and generates a display feed for outputting to one or more connected displays.

The hub 400 includes a primary processing unit 406 for managing processing of imaging data and generating display feeds using processed data, a reconfigurable hardware processor 408 for processing imaging data streams, and an auxiliary processing unit 410 for providing software-based processing of imaging data and other data.

The reconfigurable hardware processor 408 may be a Field Programmable Gate Array (FPGA) that can be reconfigured by loading hardware logic files that define circuit connections in the FPGA. The reconfigurable hardware processor 408 provides low latency and high bandwidth processing of imaging data and can be repeatedly reconfigured to provide different processing of imaging data for different imaging sessions. By leveraging a reconfigurable hardware processor, the hub 400 can provide enhanced imaging data, such as video, in real time with little or no delay between capture of imaging and display of enhanced imaging on a connected display during an imaging session. In some embodiments, the reconfigurable hardware processor 408 is a reconfigurable GPU. The primary processing unit 406 and auxiliary processing unit 410 may each be any suitable processor or combinations of processors, such as a central processing unit, a graphics processing unit, a microcontroller, an ASIC, or an FPGA any combination thereof.

The hub 400 includes memory 412, which may be a local memory located within hub 400 or may be a remote memory in a remote location that hub 400 can access through a network connection. One or more portions of memory 412 may be local and one or more portions may be remotely located. Memory 412 may include one or more configuration files 414 that specify configurations for the hub 400 for different imaging sessions, one or more software programs for executing by the primary processing unit 406 and/or the auxiliary processing unit 410, and one or more hardware logic files 418 for reconfiguring the reconfigurable hardware processor 408. The primary processing unit 406 may access a configuration file 414 to determine the processing requirements specified in the configuration file, may load a hardware logic file 418 onto the reconfigurable hardware processor 408 as defined by the configuration file, and may load a software program 416 onto the auxiliary processing unit 410 as specified in the configuration file 414. Thus, the data stored in memory 412 can be used to configure the hub 400 for different imaging sessions.

The reconfigurable hardware processor 408 is communicatively connected to the primary processing unit 406. The primary processing unit 406 may send video data streams to the reconfigurable hardware processor 408 for processing and may receive processed video back from the reconfigurable hardware processor 408 for inclusion in a display feed. The primary processing unit may load hardware logic files to the reconfigurable hardware processor 408 for reconfiguring the reconfigurable hardware processor 408.

The auxiliary processing unit 410 is communicatively coupled to the primary processing unit 406. The primary processing unit 406 may send data to the auxiliary processing unit 410 for processing and may receive the results of the processing for inclusion in a display feed. The primary processing unit 406 may load software on the auxiliary processing unit 410 for processing imaging data.

Hub 400 is configured to combine information received from multiple connected devices into a display feed for display on a connected display. Accordingly, multiple information sources can be displayed simultaneously on the connected display. Hub 400 is configured to stitch together information received from connected devices according to predefined layouts. For example, hub 400 may generate a display feed in which a first video stream is displayed in a first display section, a second video stream is displayed in a second display section, and additional information, such as data, alerts, device status, metrics, etc., is displayed in a third display section.

According to some embodiments, the primary processing unit 406 is responsible for receiving data from connected devices and stitching the data together into a composite display feed. The primary processing unit 406 may leverage the reconfigurable hardware processor 408 and/or the auxiliary processing unit 410 to process received data for enhancing display of the data.

The primary processing unit 406 combines information sources into a display feed according to one or more predefined display layouts that specify the types of imaging information to be displayed and the relative sizes and locations of imaging information and other information for display. Predefined display layouts may be associated with different types of imaging sessions, such as different types of surgical sessions or different types of surgical or other medical procedures. Different types of procedures may involve different types of imaging equipment and/or different types of imaging processing algorithms, and the predefined display layouts may specify the types of information for display for a given procedure. Predefined display layouts may be associated with different practitioners according to the preferences of the practitioners. For example, the same information may be displayed in different ways for two different practitioners performing the same procedures. Predefined display layouts may be stored as configuration data files 414 in memory 412.

Figure 5B:
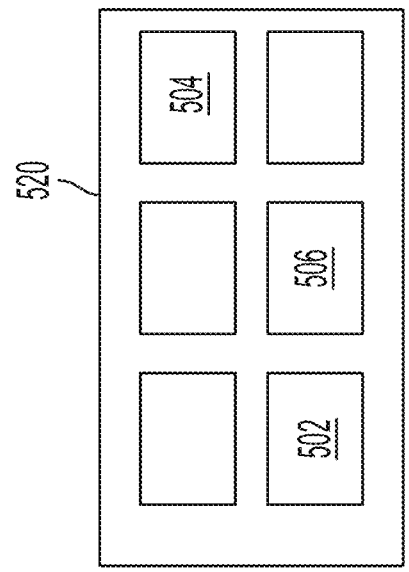
FIG. 5B illustrates an example of a second predefined display layout that can be generated by the hub of FIG. 4.
Figure 5A:
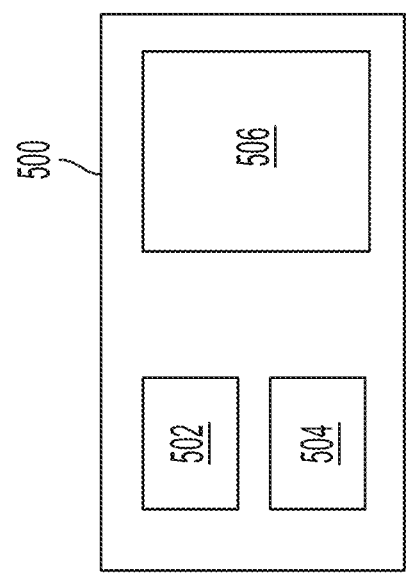
FIG. 5A illustrates an example of a first predefined display layout that can be generated by the hub of FIG. 4.

FIG. 5A illustrates an example of a first predefined display layout 500 and FIG. 5B illustrates an example of a second predefined display layout 520. The first layout 500 includes three sections for three different sources-502, 504, and 506. The term source refers to a distinct data output generated by the hub 400. Sources can include data received from one or more connected devices, enhanced data generated by processing data received from one or more connected devices, or any combination thereof. Multiple sources can include or be based on the same data received from a connected device. For example, a first source can include a video stream received from a connected device and a second source can include the same video stream enhanced with information extracted from the video stream or information received from another connected device.

In addition to defining the sources to be displayed, predefined display layouts define the relative locations of the different sources on the display and the relative sizes of the different sources on the display. For example, in first layout 500 the first source 502 is located above the second source 504 on the left half of the display, with both sources 502 and 504 being equal in size. The third source 506 is located on the right half of the display and is larger than the first and second sources. In contrast, layout 520 includes six different sources of equal size arranged in two rows of three columns. Layout 520 includes the first, second, and third sources 502, 504, and 506, in addition to three other sources. The first and second sources 502 and 504 are in different locations relative to layout 500 and the third source 506 is a different size relative to layout 500. Layout 500 may be associated with a first practitioner who configured the layout 500 according to his or her preferences and layout 520 may be associated with a second practitioner. Layouts 500 and 520 may be associated with different types of imaging sessions, such as different types of surgical procedures, or may be associated with the same type of surgical procedure. In some embodiments, both layouts are used in the same imaging session. For example, layout 500 may define the layout for a first display of an imaging system and layout 520 may define the layout for a second display of the imaging system.

The hub 400 may configure a display feed according to one or more parameters associated with an imaging session. Hub 400 may be used for multiple different types of medical procedures and/or by multiple different practitioners. As used herein, a medical procedure may refer to a single (e.g., operative) procedure with various tasks being performed by the practitioner (e.g., surgeon) or to more than one procedure being performed in a single session with a patient (e.g., a single operating session on a patient). For example, an orthopedic operating session involving performing orthopedic procedures (e.g., drilling and/or implantation of medical devices) along with an imaging procedure (e.g., to visualize the tissue space and/or blood flow/tissue perfusion) may be a single medical procedure or may be multiple medical procedures. Different types of medical procedures may utilize different types of imagers and other equipment. Display layouts designed for one type of procedure may not be as suitable for another type of procedure. Furthermore, different practitioners may have different preferences with regard to what type of information should be displayed and how the information is displayed. Accordingly, hub 400 may process received data and generate display feeds differently based on the specific requirement or preferences of each medical imaging session.

Hub 400 may configure processing of input data and generation of display feeds based on one or more predefined configurations. Predefined configurations may be associated with one or more parameters of an imaging session. Examples of imaging session parameters can include user (e.g., practitioner), procedure type, information associated with one or more connected input devices, and information associated with one or more connected output devices.

The hub 400 may receive user input (such as through user interface 114 of FIG. 1) specifying one or more parameter values and may select a predefined configuration based on the one or more parameter values. The hub 400 reconfigures processing of one or more inputs and generation of one or more display feeds based on the selected predefined configuration.

Predefined configurations may define predefined display layouts and may also define one or more data processing algorithms. Algorithms may be implemented, for example, in reconfigurable hardware processor 408 and/or in auxiliary processing unit 410. In some embodiments, the reconfigurable hardware processor 408 may be reconfigured according to the predefined configuration in order to perform imaging data processing that is specified by the predefined configuration.

As explained above, different sources can be included in different layouts. Different sources can be data from different connected devices, but can also be different information extracted from the same connected devices. To facilitate generation of different data depending on the connected devices and the layout preferences from one imaging session to the next, hub 400 may automatically reconfigure the processing of data received from connected devices according to the requirement specified in the configuration data associated with an imaging session.

Hub 400 may receive an indication of an imaging session that is associated with a predefined configuration and may automatically configure processing of input data and generation of display feeds accordingly. For example, in preparation for a surgical session, a nurse may input one or more parameters associated with the surgical session to the hub 400, such as through a keyboard, mouse, touchscreen, or other input device, and the hub 400 may configure itself accordingly, which may include reconfiguring the reconfigurable hardware processor by loading one or more hardware logic files stored in memory 412 and loading one or more software programs or modules on auxiliary processing unit 410. Parameters can include the type of surgery to be performed and the practitioner performing the surgery. One or more predefined layouts may be associated with the type of surgery and/or the practitioner and the hub 400 may reconfigure itself to generate a display feed according to the predefined layout.

Figure 6:
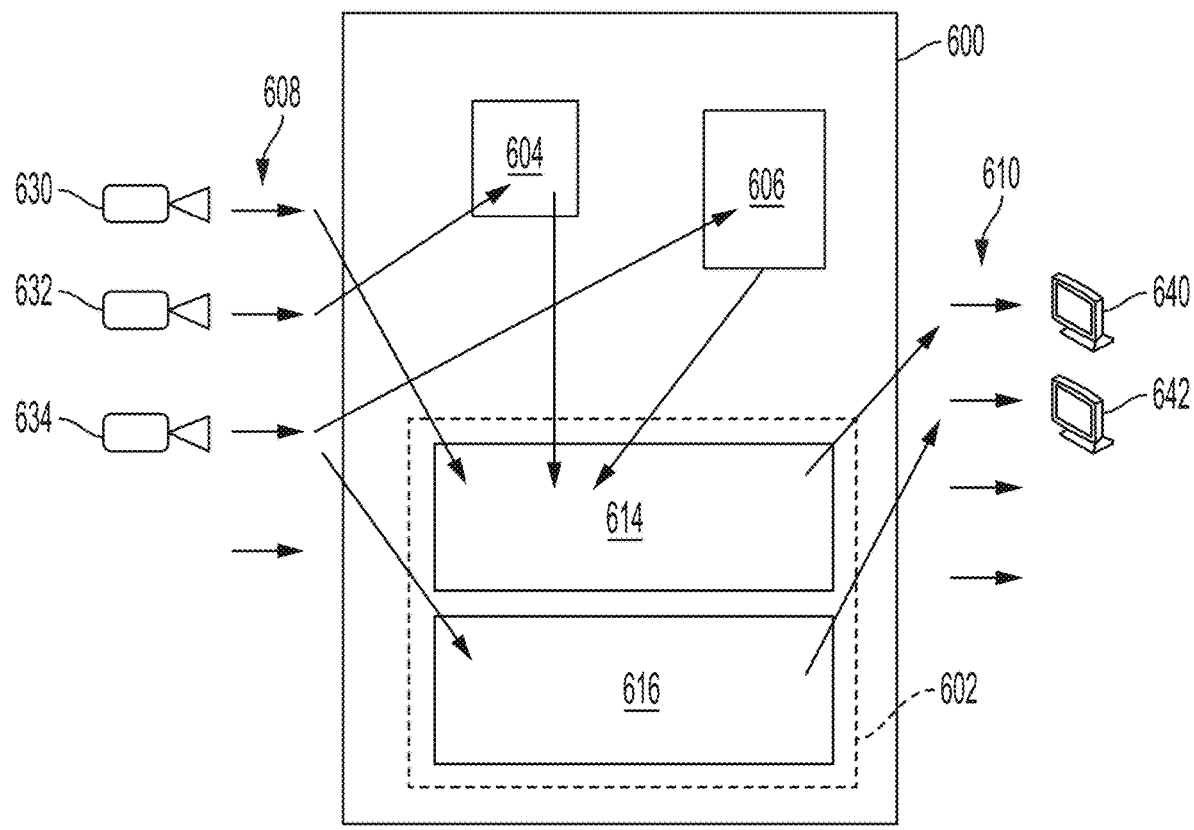
FIG. 6 illustrates an example of a medical imaging processing hub configured for a first imaging session, according to some embodiments.

FIG. 6 illustrates an example of a medical imaging processing hub, such as a hub 400, configured for a first imaging session. Configured hub 600 includes a primary processor 602, a reconfigurable hardware processor 604, and an auxiliary processor 606. Hub 600 includes multiple data inputs 608, three of which are connected to three different devices (630, 632, and 634), which can be cameras, camera control units, instrument control units, lighting control units, insufflators, cauterizers, or any other device or system used during the imaging session that generates data relevant to the imaging session. Hub 600 includes multiple video outputs 610. In the illustrated embodiment, two displays 640 and 642 are connected to two of the video outputs 610.

In the first configuration, one or more algorithms have been loaded into the reconfigurable hardware processor 604 for processing imaging data received from device 632. The reconfigurable hardware processor 604 processes data received from device 632 and transmits the processed data to the primary processor 602. The reconfigurable hardware processor 604 may receive imaging data directly from the input 608 or may receive data via the primary processor 602. In some embodiments, the primary processor 602 may crop image data, according to the principles described above with respect to method 200 of FIG. 2, and provide the cropped image data to the reconfigurable hardware processor 604 and/or to the auxiliary processor 606. This may be advantageous in reducing the amount of imaging data requiring processing.

The auxiliary processor 606 executes a software based program for processing data from the third connected device 634. The auxiliary processor 606 may output the results of the processing to the primary processor 602 via, for example, a video output 612, such as a video output on the mother board for the CPU.

The primary processor 602 is responsible for combining the different data sources into a display feed for transmission to the connected display 640. The primary processor stiches together the processed data from the reconfigurable hardware processor 604, from the auxiliary processor 606, and directly from a first connected device 630. For example, the primary processor may generate a display feed that locates these three sources into different sections of the display.

In some embodiments, the primary processor 602 may be configured to provide multiple different display streams. In the illustrated embodiment, the primary processor 602 includes two compositors 614 and 616 that can generate two different display feeds, according to, for example, configuration data stored in memory. The first compositor 614 is configured to combine the data from the first connected device, the reconfigurable hardware processor 604, and the auxiliary processor 606 into a first display feed for transmission to display 640. The second compositor 616 receives data input (e.g., video input) from device 634 and generates a second display feed for transmission to display 642.

The compositors may combine data sources and generate display feeds differently from one imaging session to the next. The handling of data by the compositors may be altered based on configuration data stored in memory. For example, the data handling illustrated in FIG. 6A may be defined by a first configuration file. A second configuration file may specify alteration of this data handling by, for example, specifying that the first compositor 614 generate a display feed based on data from only the first device 630 for display on the first display 640 and the second compositor 616 generate a display feed based on data from device 632 and device 634 for display on the second display 642. The different configurations may be associated with different types of procedures and/or different practitioners to, for example, support different imaging sessions.

Figure 7:
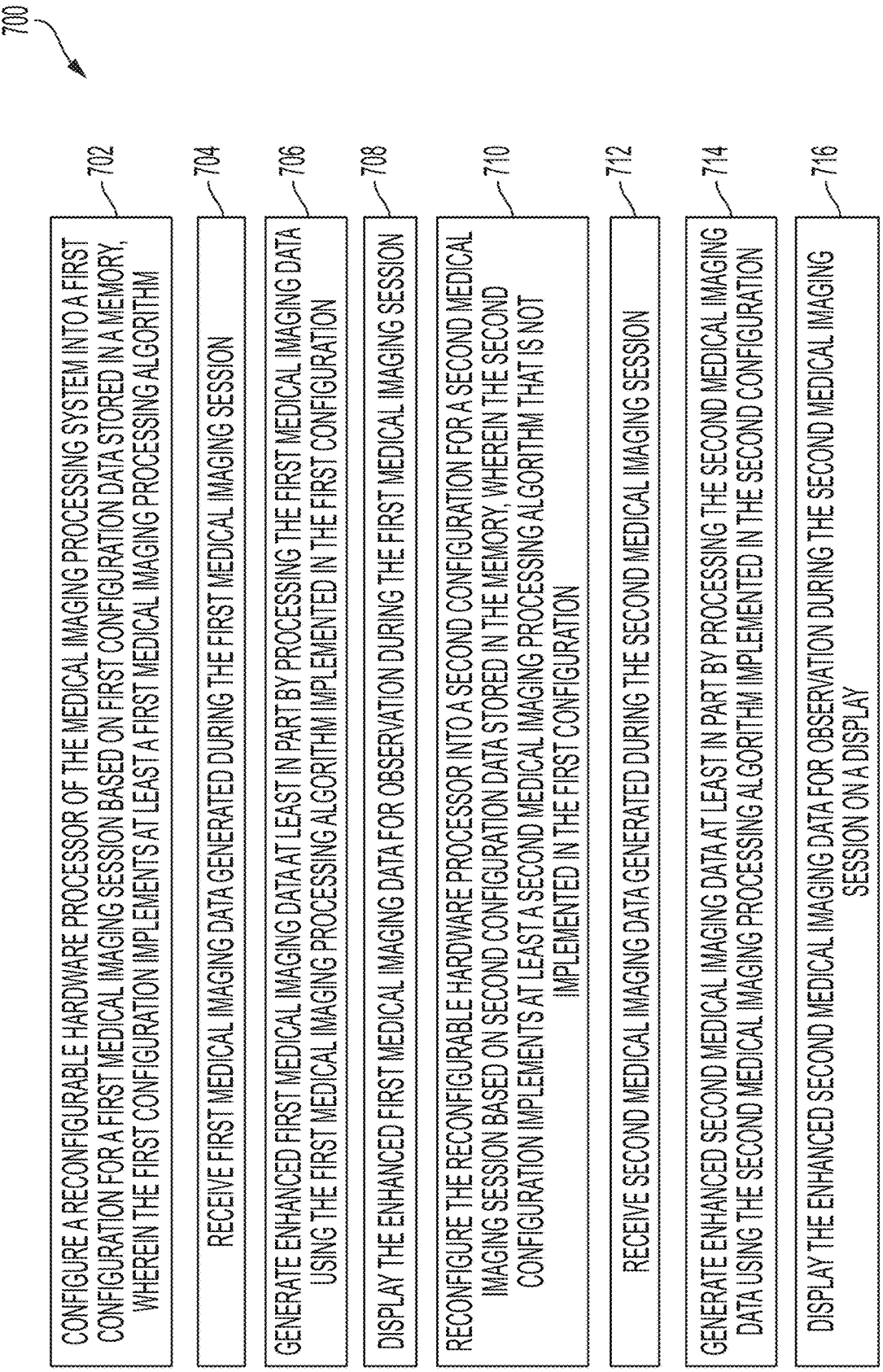
FIG. 7 illustrates a method for configuring a medical imaging processing system, according to some embodiments.

FIG. 7 illustrates a method 700 for configuring a medical imaging processing system, such as hub 400, according to some embodiments. As described further below, method 700 includes reconfiguring a reconfigurable hardware processor, such as reconfigurable hardware processor 408 of hub 400, according to predefined configuration data associated with a medical imaging session. The reconfigurable hardware processor is configured to implement imaging data processing algorithms defined by the configuration data. Leveraging a reconfigurable hardware processor to implement imaging processing algorithms allows for a hardware processor configuration that is tailored to processing of imaging data according to the specified algorithms and allows for different algorithms to be implemented for different imaging sessions having different imaging inputs and/or display requirements. Accordingly, the reconfigurable hardware processor can provide advantages over a general purpose processor running software-based algorithms, which may not be able to provide the lower latency and higher bandwidth that the reconfigurable processor can provide, which are important in providing real time processing of video for display during a medical procedure.

At step 702, a reconfigurable hardware processor, such as reconfigurable hardware processor 408 of hub 400, is configured into a first configuration for a first medical imaging session. The configuration of the hardware processor may be based on first configuration data stored in memory. The first configuration data may define one or more medical imaging processing algorithms for implementation by the reconfigurable hardware processor. Once configured into the first configuration, the reconfigurable hardware processor implements the one or more medical imaging processing algorithms as defined in the configuration data. The reconfigurable hardware processor may be configured by loading one or more hardware logic files from memory (which may be handled by a second processor, such as primary processing unit 406 of hub 400) onto the reconfigurable hardware processor.

The first imaging session may include the performance of one or more medical procedures, such as surgical procedures, on a patient. The first imaging session may begin with a nurse or other user initializing the medical imaging system for a medical procedure or series of medical procedures on a patient. The first medical imaging session may be complete when the medical procedure or all of a series of medical procedures on a patient are complete or may be complete when a first of a series of procedures on a patient are complete. As an example of this latter scenario, a first medical procedure on a patient, such as a first surgical procedure may complete, which completes a first imaging session, and a second medical procedure, such as a different surgical procedure by the same or a different surgeon, may follow. The second medical procedure may include a second imaging session.

The reconfigurable hardware processor, in its first configuration, is configured to receive medical imaging data and to process at least a portion of the data using the first imaging processing algorithm. In some embodiments, the first configuration may also include the ability to process the received data using one or more additional processing algorithms. The reconfigurable hardware processor in the first configuration may have the ability to process multiple distinct sets of imaging data (e.g., generated by different devices) using the first imaging processing algorithm and/or additional imaging processing algorithms. For example, the reconfigurable hardware processor in the first configuration may receive a first set of data generated by a first connected device and may process the first set of data using the first medical imaging processing algorithm and may also receive a second set of data generated by a second connected device and may process the second set of data using a second medical imaging processing algorithm.

In some embodiments, the reconfigurable hardware processor is configured in response to an input indicative of the first medical imaging session. For example, a user, such as an operating room nurse, may provide information to the medical imaging processing system specifying parameters associated with the imaging session, such as medical procedure type and/or practitioner identity. The one or more parameters may be associated with the first configuration data and the system may access the first configuration data and configure the reconfigurable hardware processor according to the specification of the first configuration data. User input indicative of the first medical imaging session may include a user selection of a profile. The profile may be associated with one or more types of medical procedures and may define data processing and display layout tailored to the one or more types of medical procedures. Types of medical procedure can include endoscopic medical procedures, such as an enteroscopy, a colonoscopy, a sigmoidoscopy, a rectoscopy, a rhinoscopy, a otoscopy, a cystoscopy, a colposcopy, a arthroscopy, a thoracoscopy, etc., and surgical procedures, such as a biopsy, a carotid endarterectomy, a cholecystectomy, a coronary artery bypass, a skin graft, a hysterectomy, and a mastectomy.

The profile may be a practitioner profile that defines the types of data that the practitioner wants to see in the layout that the practitioner prefers. The profile may be a default profile that includes a predefined layout and predefined data processing. The default profile may be based on one or more parameters of the medical imaging system that are detected by the medical imaging processing system, such as number and types of inputs to the processing system and number and types of display outputs from the processing system. In some embodiments, default profile may be based on one or more parameters detected from received image data, such as a radius or diameter of an FOV, which may be associated with a type of imager (e.g., an endoscope size).

At step 704, the system receives first medical imaging data generated during the first medical imaging session. The first medical imaging data is received from one or more devices connected to one or more inputs of the system. For example, the first medical imaging data may be a series of video frames received from an imager, such as an endoscopic imager. The first medical imaging data may include data from multiple devices connected to the system, such as multiple video feeds from multiple imagers.

At step 706, enhanced first medical imaging data is generated at least in part by processing the first medical imaging data using the first medical imaging processing algorithm implemented by the reconfigurable hardware processor in the first configuration. The reconfigurable hardware processor processes at least a portion of the first medical imaging data using the first medical imaging processing algorithm and any other algorithms that the reconfigurable hardware processor is configured to implement, as defined by the first configuration data. For example, in the first configuration, the reconfigurable hardware processor may implement a smoke detection algorithm that detects portions of received images associated with smoke in the field of view and enhances the received images to reduce the appearance of smoke.

Some or all of the first medical imaging data may be routed to the reconfigurable hardware processor by, for example, a primary processor, such as primary processing unit 406 of hub 400. The primary processor may receive the first medical imaging data and may route the data to the reconfigurable processor according to the first configuration data. The first configuration data may specify that data received from a connected device should be processed using at least the first medical imaging processing algorithm. In accordance with this requirement, the primary processor may direct data received from the connected device to the reconfigurable hardware processor. In some embodiments, the reconfigurable processor receives the first medical imaging data directly from the input connection to the connected device—i.e., without the data first being routed through one or more additional processing units.

Processing of data by the reconfigurable hardware processor may be based on processing by other processing units of the system. For example, processing of the first medical imaging data by the first medical imaging processing algorithm may be based on information received from a second processing unit. The second processing unit may analyze some or all of the first medical imaging data and the results of the analysis may be used by the reconfigurable hardware processor in the implementation of the first medical imaging processing algorithm. For example, in the embodiment implementing a smoke detection algorithm in the reconfigurable processor discussed above, an auxiliary processing unit, such as auxiliary processing unit 410 of hub 400, may receive some or all of the first imaging data to determine whether smoke is present in the imaged field of view. Upon detecting smoke, the auxiliary processing unit may notify the reconfigurable hardware processor (either directly or via another processing unit, such as primary processing unit 406) and, in response, the reconfigurable hardware processor may begin processing the first imaging data to reduce the contribution of smoke in the data.

At step 708, the enhanced first medical imaging data generated by the reconfigurable hardware processor is displayed for observation during the first medical imaging session. For example, the first medical imaging session may include an endoscopic procedure that involves the use of a cauterizing tool and the enhanced first medical imaging data may be an enhancement of a video feed generated by an endoscopic camera in which the appearance of smoke generated by the cauterizing tool has been reduced. This enhanced imaging may be displayed to the surgeon in real time so that the surgeon can better visualize the surgical field.

In some embodiments, the enhanced first medical imaging data is received from the reconfigurable hardware processor by another processing unit, such as primary processing unit 406 of hub 400. The primary processor may generate one or more display feeds that include the enhanced first medical imaging data. The primary processor may generate the one or more display feeds based at least in part on the first configuration data. For example, the primary processor may combine the enhanced first medical imaging data with additional information, such as additional imaging received from another connected device, for display in different parts of a display as defined by the first configuration data.

In some embodiments, the display feed includes the enhanced first medical imaging data combined with other data. For example, the display feed may include the enhanced first medical imaging data for display in a first portion of a connected display and may include additional information for display in a second portion of the connected display. In some embodiments, the system generates multiple display feeds having different display configurations for displaying the enhanced imaging data and provides different display feeds to different displays.

Figure 8A:
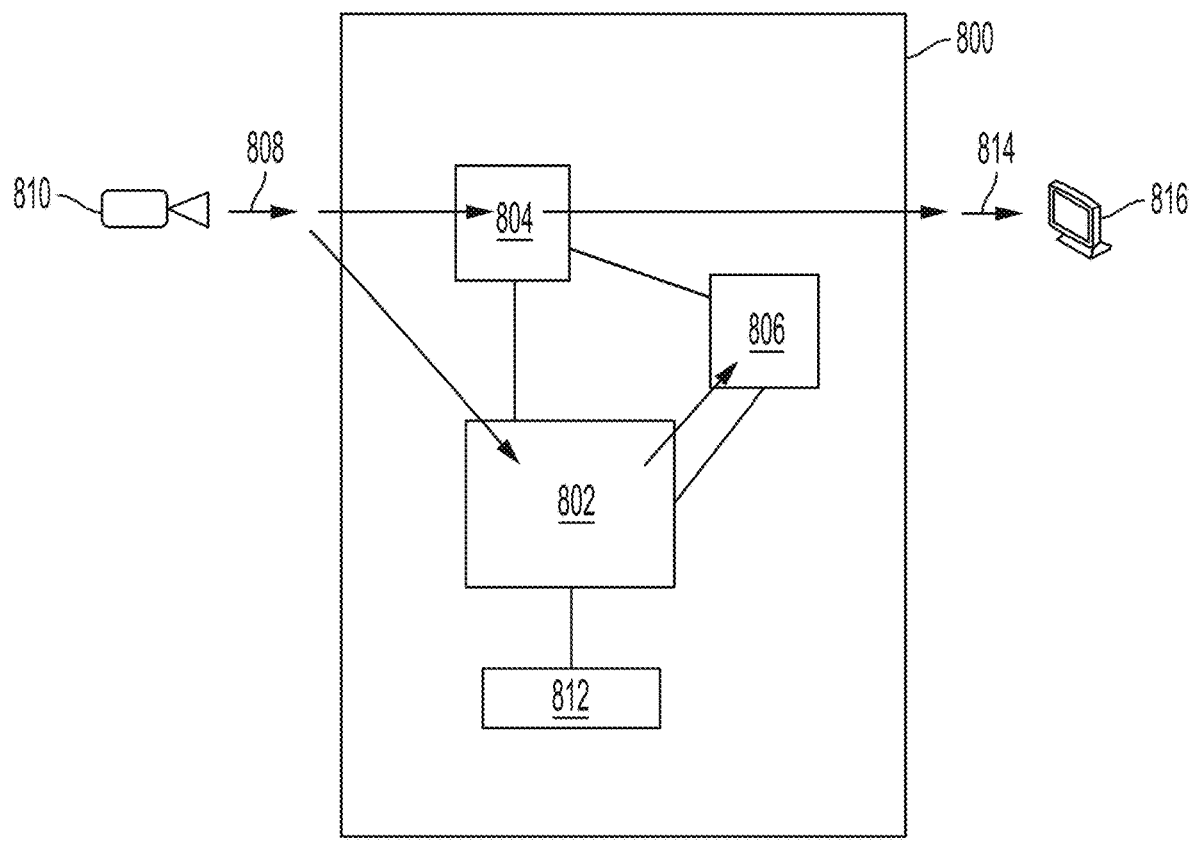
FIGS. 8A and 8B are block diagrams of a medical imaging processing system performing the method of FIG. 7, according to one embodiments.
Figure 8B:
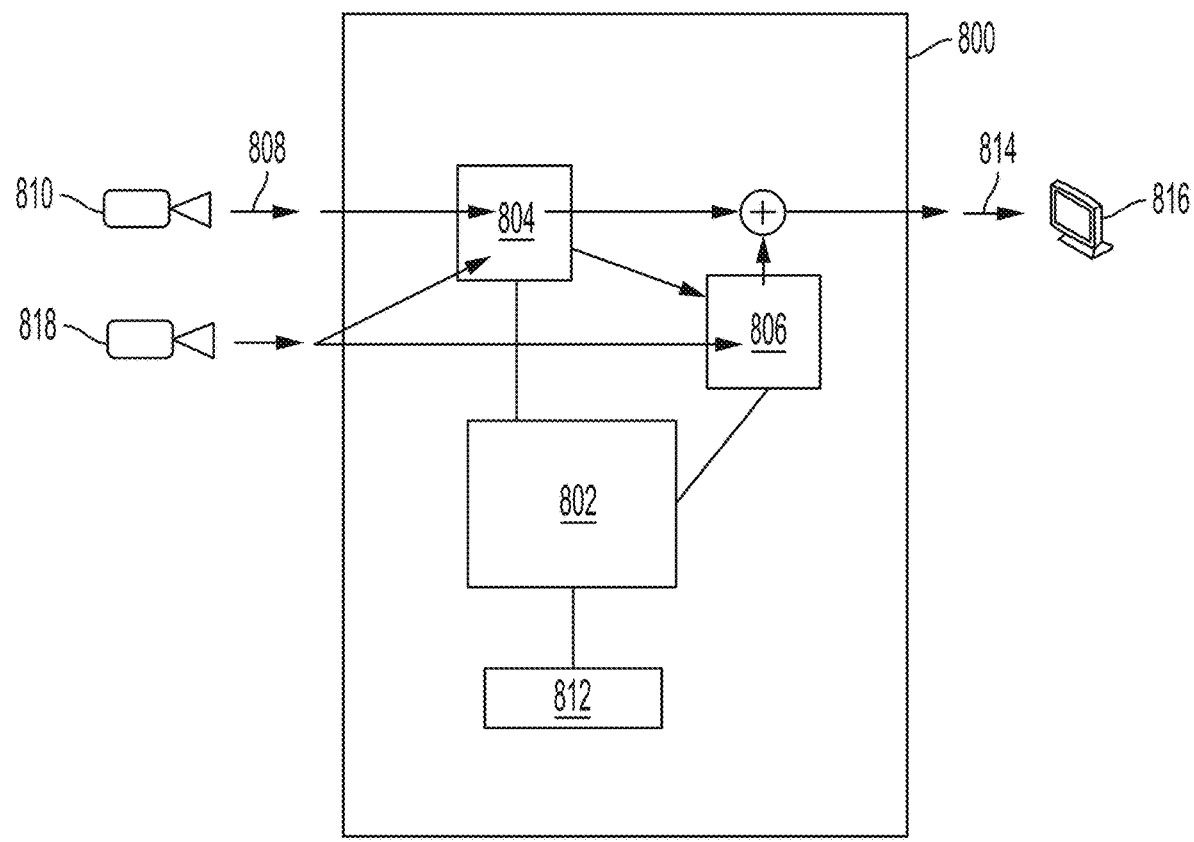

FIG. 8A is a block diagram of a medical imaging processing system 800 illustrating steps 702-708 of method 700, according to one embodiment. Reconfigurable hardware processor 804 is configured to process imaging data received from a white light imager 810 via a first input port 808 using a first imaging processing algorithm, such as a smoke detection and removal algorithm. In response to a user input associated with a first imaging session, the primary processor 802 accessed first configuration data stored in the memory 812, and based on the specifications in the first configuration data, the primary processor 802 reconfigured reconfigurable hardware processor 804 by loading a hardware logic configuration file for a smoke reduction algorithm. In addition, the primary processor 802 loaded a smoke detection software program or module from the memory 812 to the auxiliary processor 806. The auxiliary processor 806 running the smoke detection software program or module can detect the presence of smoke in received imaging data and can instruct the reconfigurable hardware processor 804 to process the imaging data to reduce the influence of smoke in the imaging data. Prior to detection of smoke by the auxiliary processor 806, the reconfigurable hardware processor may simply pass imaging data through for display without first processing the data for smoke removal. The primary processor may provide the auxiliary processor 806 with one or more portions of the received imaging data (such as one or more frames), such as on a periodic basis, for detecting smoke and triggering the smoke removal processing of the reconfigurable hardware processor 804. The system 800 outputs a display feed to display 816 that includes imaging data received from the white light imager 810 that has been enhanced by removing contributions from smoke when smoke is detected in the imaging data.

Returning to method 700, at step 710, the reconfigurable hardware processor is reconfigured into a second configuration for a second medical imaging session based on second configuration data stored in the memory. The second configuration implements at least one medical imaging processing algorithm that is not implemented in the first configuration.

In some embodiments, the reconfigurable hardware processor is reconfigured in response to an input indicative of the second medical imaging session. For example, a user, such as an operating room nurse, may provide information to the medical imaging processing system specifying parameters associated with the second imaging session, such as medical procedure type and/or practitioner identity. The one or more parameters may be associated with the second configuration data and the system may access the second configuration data and configure the reconfigurable hardware processor according to the specifications of the second configuration data. User input indicative of the second medical imaging session may include a user selection of a profile, as discussed above. Depending on the profile selected, the second imaging session may be associated with the same practitioner as the first imaging session—for example, where the same practitioner is transitioning from one type of medical procedure to another type of medical procedure that may require different display layouts, such as due to different equipment connected to the medical imaging processing system or different enhancement algorithms. The second imaging session may be associated with the same type of medical procedure but different practitioners. For example, a first surgeon may perform a type of surgery (e.g., a cholecystectomy) on a first patient in the first imaging session and a second surgeon may perform the same type of surgery (e.g., a cholecystectomy) on a second patient (e.g., later in the day or on a following day).

The first imaging session may have completed (e.g., the surgery or procedure associated with the first imaging session has completed) and the imaging system may be set up for use in the subsequent second imaging session. The second imaging session may involve one or more different types of procedures and/or may include one or more different users for which different imaging processing may be beneficial. Accordingly, the second configuration implements one or more image processing algorithms that were not implemented in the first imaging session. The reconfigurable hardware processor is reconfigured to implement the one or more image processing algorithms that are required for the second imaging session, as defined by the second configuration data.

In some embodiments, the second imaging session may be a second surgical session for which the imaging system is to be used. After completion of the first imaging session, the operating room may be set up for the second surgical session. The second surgical session may involve a different type of surgery, a different practitioner, a different patient, etc. During set up for the second surgical session, the imaging processing system may receive an input indicative of the second surgical session. The input can be, for example, a selection of a type of surgical procedure or a selection of a profile (e.g., a practitioner profile) that is made via a user interface to the imaging processing system. Based on this selection, the system may automatically reconfigure the reconfigurable processor based on the configuration data associated with the second surgical session.

At step 712, the medical imaging processing system receives second medical imaging data generated during the second medical imaging session. This second medical imaging data may be received from the same connected device or devices as the first medical imaging data or from a different connected device or devices.

At step 714, enhanced second medical imaging data is generated at least in part by processing the second medical imaging data using the second medical imaging processing algorithm implemented in the second configuration of the reconfigurable hardware processor. The reconfigurable hardware processor processes at least a portion of the first medical imaging data using the second medical imaging processing algorithm (which was not implemented in the first configuration) and any other algorithms that the reconfigurable hardware processor was configured to implement, which may or may not have been implemented in the first configuration, as defined by the second configuration data. For example, in the second configuration, the reconfigurable hardware processor may implement an algorithm that processes fluorescence images (e.g., video frames) to determine one or more features of blood flow through tissue, such as tissue perfusion, blood vessel location, blood flow amounts or rates, dimensions of imaged tissue, or any combinations thereof, and generates enhanced imaging modifying the fluorescence images according to the determined features (modifying coloring of the images, overlaying data on the images, overlaying contouring on the images, etc.).

As in the first configuration described above, some or all of the second medical imaging data may be routed to the reconfigurable hardware processor by, for example, a primary processor, such as primary processing unit 406 of hub 400. The primary processor may receive the second medical imaging data and may route the data to the reconfigurable processor according to the second configuration data. The second configuration data may specify that data received from a connected device should be processed using at least the second medical imaging processing algorithm. In accordance with this requirement, the primary processor may direct data received from the connected device to the reconfigurable hardware processor. In some embodiments, the reconfigurable processor receives the first medical imaging data directly from the input, i.e., without the data first being routed through one or more additional processing units.

At step 716, the enhanced second medical imaging data generated by the reconfigurable hardware processor is displayed for observation during the second medical imaging session. Display of the enhanced second medical imaging data can assist a practitioner, such as a surgeon, during one or more procedures performed during the second medical imaging session. By leveraging the low latency and high bandwidth of the reconfigurable processor, the enhanced second medical imaging data can be displayed in real time.

In some embodiments, the enhanced second medical imaging data may be transmitted from the reconfigurable hardware processor to another processing unit, such as the primary processing unit 406 of FIG. 4, which may generate a display feed that includes the enhanced second medical imaging data. The display feed may be transmitted by the primary processor to one or more connected displays. In some embodiments, the reconfigurable hardware processor may transmit the enhanced second medical imaging data directly to an output connection with one or more connected displays.

FIG. 8A is a block diagram of a medical imaging processing system 800 illustrating steps 710-716 of method 700, according to one embodiment. Reconfigurable hardware processor 804 is reconfigured to process imaging data received from the white light imager 810 and a fluorescent imager 818 (these may be portions of the same imaging system and may be received on the same or different input ports) using a second imaging processing algorithm that analyzes the fluorescence imaging to characterize portions of tissue according to, for example, the health of the tissue, extent of blood flow in the tissue, or extent of perfusion in the tissue and overlays the characterization on the white light imaging. In response to a user input associated with a second imaging session (e.g., an input indicating a surgical session on a new patient or indicating a new procedure on the same patient as the first imaging session), the primary processor 802 accessed second configuration data stored in the memory 812, and based on the specifications in the first configuration data, the primary processor 802 reconfigured reconfigurable hardware processor 804 by loading a hardware logic configuration file for the tissue characterization algorithm. In addition, the primary processor 802 loaded a reference marker software program or module from the memory 812 to the auxiliary processor 806. The auxiliary processor 806 running the reference marker program or module can determine locations of, for example, maximum and/or minimum perfusion in the fluorescence imaging data. Reference markers generated by the auxiliary processor 806 are added to the overlay generated by the reconfigurable hardware processor (this may be done by the reconfigurable hardware processor 804, by the primary processor 802, or by a different processor of the system). The resulting enhanced imaging data is output to display 816 for visualization during the second imaging session.

According to some embodiments, the tissue characterization algorithm implemented in the reconfigurable hardware processor may provide enhanced visual representations of tissue of a subject that may be more accurate in terms of data representation, and intuitive for clinicians to use for their clinical decision making. The enhanced visual representations of tissue generated may be applicable to various types of tissue (e.g. a variety of wounds including chronic, acute, pressure ulcers, cancerous tissue), and may provide a framework for automatically classifying the tissue (e.g., wound tissue, cancerous tissue) and/or predicting clinical outcomes (e.g., healing timeline for wound tissue, healing of cancerous tissue).

The tissue characterization algorithm may utilize machine learning or deep learning. Machine learning-based methods and systems facilitate solving problems that either do not have an algorithmic solution or a solution is too complex to find. Medical diagnosis and tissue characterization based on imaging of the tissue is a task particularly well suited for machine learning algorithms due to complex nature of physiological processes taking place in the human body. Machine learning can be used to discover medically-relevant features and patterns within large datasets and help clinicians make medical diagnoses more accurately, more quickly and more consistently irrespective of the clinician's experience. In some embodiments, the tissue characterization algorithm includes identifying one or more attributes of the data that are relevant to a clinical characterization of the tissue, and categorizing the data into a plurality of clusters based on the one or more attributes of the data such that the data in the same cluster are more similar to each other than the data in different clusters, wherein the clusters characterize the tissue. In some variations, the algorithm may further include associating a respective cluster with each of a plurality of subregions in a time series of images such as for example fluorescence images, and generating a subject spatial (cluster) map based on the associated clusters for the plurality of subregions in the subject time series of fluorescence images. The algorithm may further include receiving a plurality of subject spatial maps and receiving metadata associated with each subject spatial map, storing each subject spatial map and its associated clinical data in a record of a database, and using the records of the database as input for a supervised machine learning algorithm for generating a predictive model. The predictive model may be used for predicting clinical data associated with the subject time series of fluorescence images of the subject.

Figure 9A:
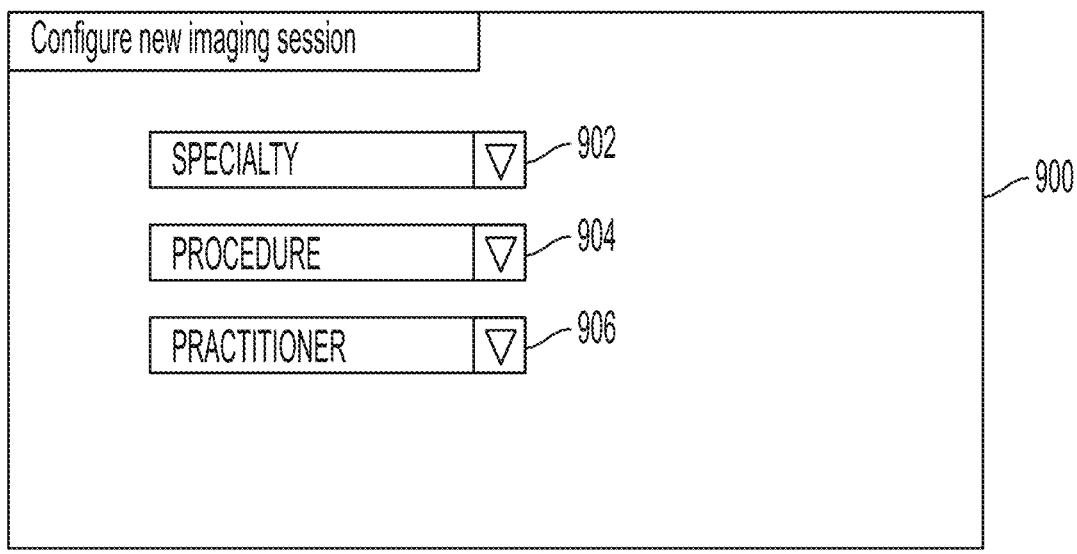
FIGS. 9A and 9B illustrate graphical user interfaces for configuring a medical imaging processing system for a new imaging session, according to some embodiments.
Figure 9B:
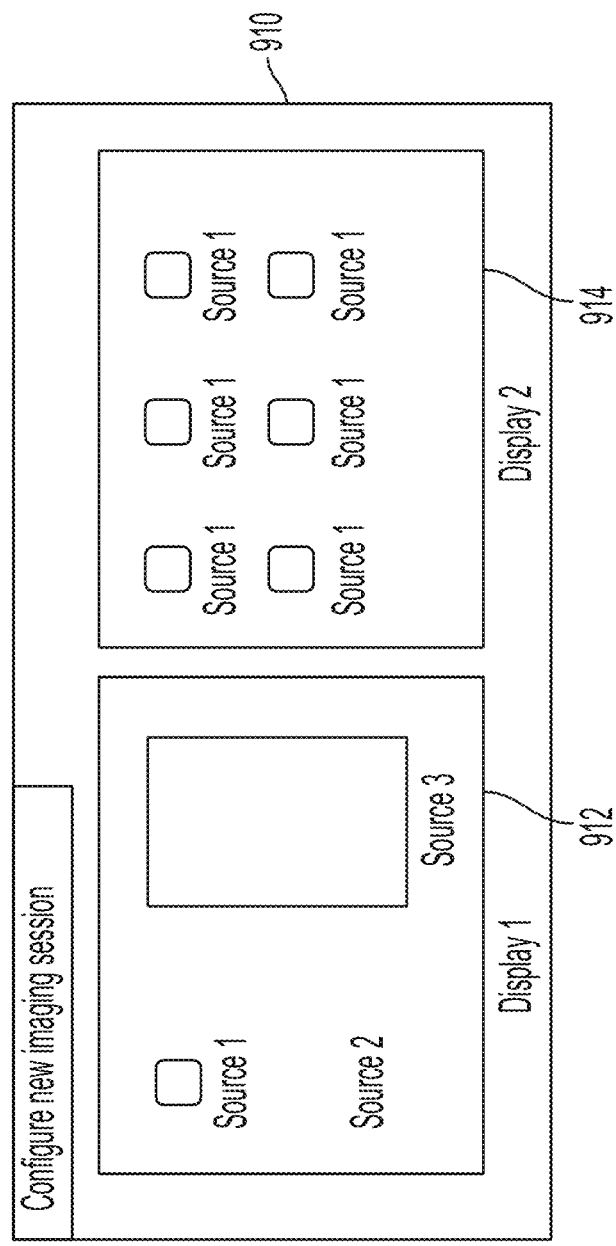

FIGS. 9A and 9B illustrate graphical user interfaces for configuring a medical imaging processing system, such as hub 400, for a new imaging session. The user interfaces may be provided, for example, on a tablet connected to the system or on a touchscreen of the system. User interface 900 of FIG. 9A enables a user to configure an imaging processing system by selecting a specialty 902, a procedure 904, and/or a practitioner 906. Each selection may be associated with a different configuration or combinations of selections may be associated with configurations. For example, each practitioner selection may be associated with a different configuration, which has been previously specified by the practitioner, whereas selection of both a specialty and a procedure may be required to select a configuration. Configurations may be stored locally in memory of the system or remotely in, for example, a hospital information system, which is access, for example, via a network connection.

FIG. 9B illustrates a user interface 910 for defining data sources and data source layouts. Two display layouts (912 and 914) are associated with the illustrated configuration. Each of the display layouts defines data sources and data source size and location. The first display layout 912 includes three different sources. As described above, sources can define types of data displayed, which can be based on both the system that generates data and the types of processing on the data performed, for example, by the reconfigurable processor and/or other system modules. As such, different sources may be based on data from the same imaging system or other devices. For example, source 1 can be still images from an input video stream (e.g., as selected via voice commands from a practitioner) and source 3 can be the video stream. User interface 910 may enable a user to select, position, and size different sources. For example, the user can select available sources from a drop-down list that specifies, for example, all sources that the system is able to generate or all sources that the system is able to generate given the inputs to the system. A user can drag source icons around the screen to reposition the sources and can resize sources using, for example, gestures, mouse inputs, keyboard inputs, or any other suitable input.

Once a user completes selection of a configuration profile, the medical imaging processing system may automatically configure itself according to the requirements defined in the selected configuration profile, according to the methods described above.

Figure 10:
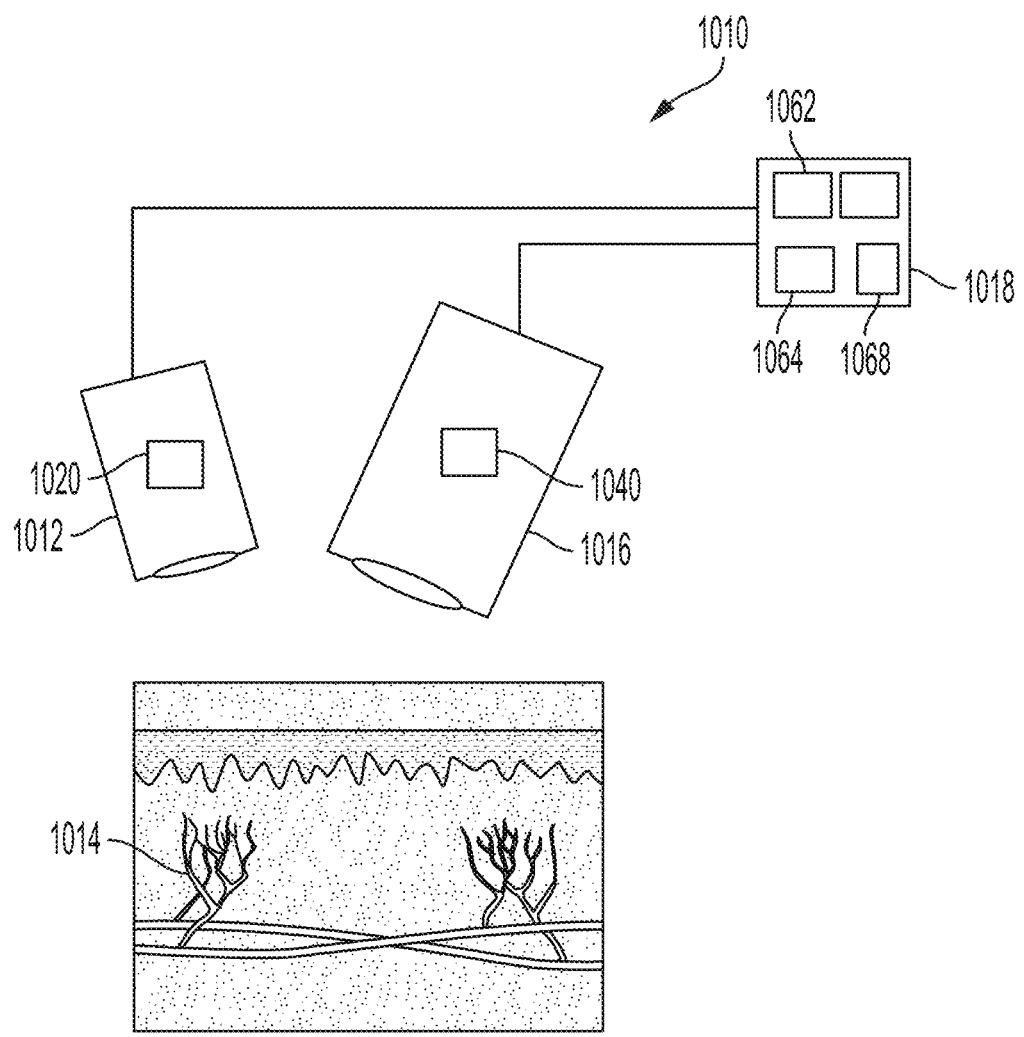
FIG. 10 is an illustrative depiction of an exemplary fluorescence imaging system, according to some embodiments.

A system for collecting, enhancing, and displaying medical imaging data, such as system 100 of FIG. 1, may include one or more imaging systems for acquiring a time series of images of tissue (e.g., a time series of fluorescence images, a time series of white light images, etc.). In some embodiments, an imaging system is a fluorescence imaging system. FIG. 10 is a schematic example of a fluorescence imaging system 1010, according to one embodiment. The fluorescence imaging system 1010 comprises a light source 1012 to illuminate the tissue of the subject to induce fluorescence emission from a fluorescence imaging agent 1014 in the tissue of the subject (e.g., in blood, in urine, in lymph fluid, in spinal fluid or other body fluids or tissues), an image acquisition assembly 1016 arranged for generating the time series and/or the subject time series of fluorescence images from the fluorescence emission, and a processor assembly 1018 arranged for processing the generated time series/subject time series of fluorescence images according to any of the variations of the methods described herein. The processor assembly 1018 may include memory 1068 with instructions thereon, a processor module 1062 arranged for executing the instructions on memory 1068 to process the time series and/or subject time series of fluorescence images, and a data storage module 1064 to store the unprocessed and/or processed time series and/or subject time series of fluorescence images. In some variations, the memory 1068 and data storage module 1064 may be embodied in the same storage medium, while in other variations the memory 1068 and the data storage module 1064 may be embodied in different storage mediums. The system 1010 may further include a communication module 1066 for transmitting images and other data, such as some or all of the time series/subject time series of fluorescence images or other input data, spatial maps, subject spatial maps, and/or a tissue numerical value (quantifier), to an imaging data processing hub, such as imaging data processing hub 102 of FIG. 1, according to the systems and methods discussed above.

Figure 11:
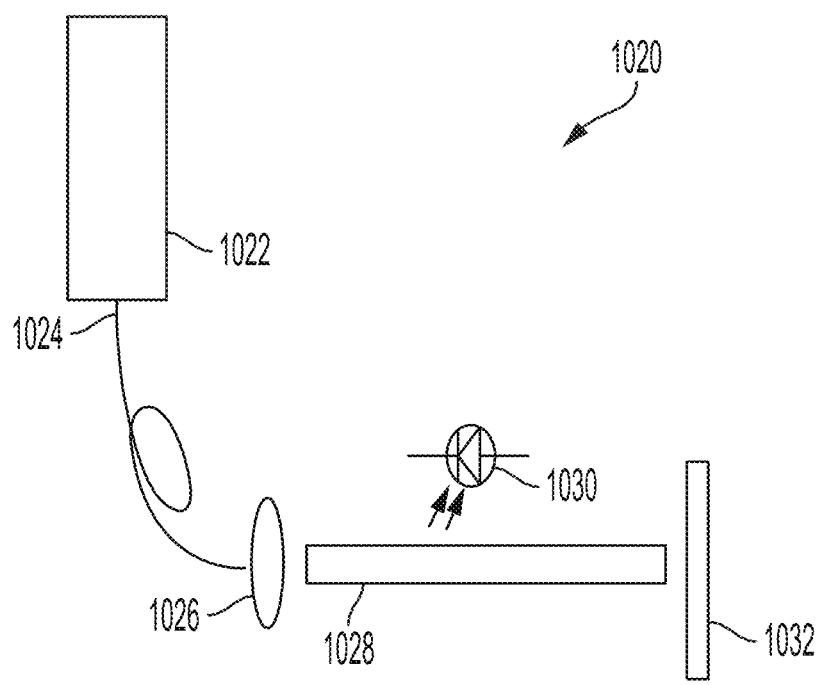
FIG. 11 is an illustrative depiction of an exemplary illumination module of a fluorescence imaging system, according to some embodiments.

In some variations, the light source 1012 includes, for example, an illumination module 1020. Illumination module 1020 may include a fluorescence excitation source arranged for generating an excitation light having a suitable intensity and a suitable wavelength for exciting the fluorescence imaging agent 1014. As shown in FIG. 11, the illumination module 1020 may comprise a laser diode 1022 (e.g., which may comprise, for example, one or more fiber-coupled diode lasers) arranged for providing an excitation light to excite the fluorescence imaging agent (not shown) in tissue of the subject. Examples of other sources of the excitation light which may be used in various embodiments include one or more LEDs, arc lamps, or other illuminant technologies of sufficient intensity and appropriate wavelength to excite the fluorescence imaging agent in the tissue. For example, excitation of the fluorescence imaging agent in blood, wherein the fluorescence imaging agent is a fluorescence dye with near infra-red excitation and emission characteristics, may be performed using one or more 793 nm, conduction-cooled, single bar, fiber-coupled laser diode modules from DILAS Diode Laser Co, Germany.

In some variations, the light output from the light source 1012 may be projected through one or more optical elements to shape and guide the output being used to illuminate the tissue area of interest. The optical elements may include one or more lenses, light guides, and/or diffractive elements so as to ensure a flat field over substantially the entire field of view of the image acquisition assembly 1016. The fluorescence excitation source may be selected to emit at a wavelength close to the absorption maximum of the fluorescence imaging agent 1014 (e.g., indocyanine green (ICG), etc.). For example, as shown in FIG. 11, the output 1024 from the laser diode 1022 may be passed through one or more focusing lenses 1026, and then through a homogenizing light pipe 1028 such as, for example, light pipes commonly available from Newport Corporation, USA. Finally, the light may be passed through an optical diffractive element 1032 (i.e., one or more optical diffusers) such as, for example, ground glass diffractive elements also available from Newport Corporation, USA. Power to the laser diode 1022 may be provided by, for example, a high-current laser driver such as those available from Lumina Power Inc. USA. The laser may optionally be operated in a pulsed mode during the image acquisition process. An optical sensor such as a solid state photodiode 1030 may be incorporated into the illumination module 1020 and may sample the illumination intensity produced by the illumination module 1020 via scattered or diffuse reflections from the various optical elements. In some variations, additional illumination sources may be used to provide guidance when aligning and positioning the module over the area of interest.

Figure 12:
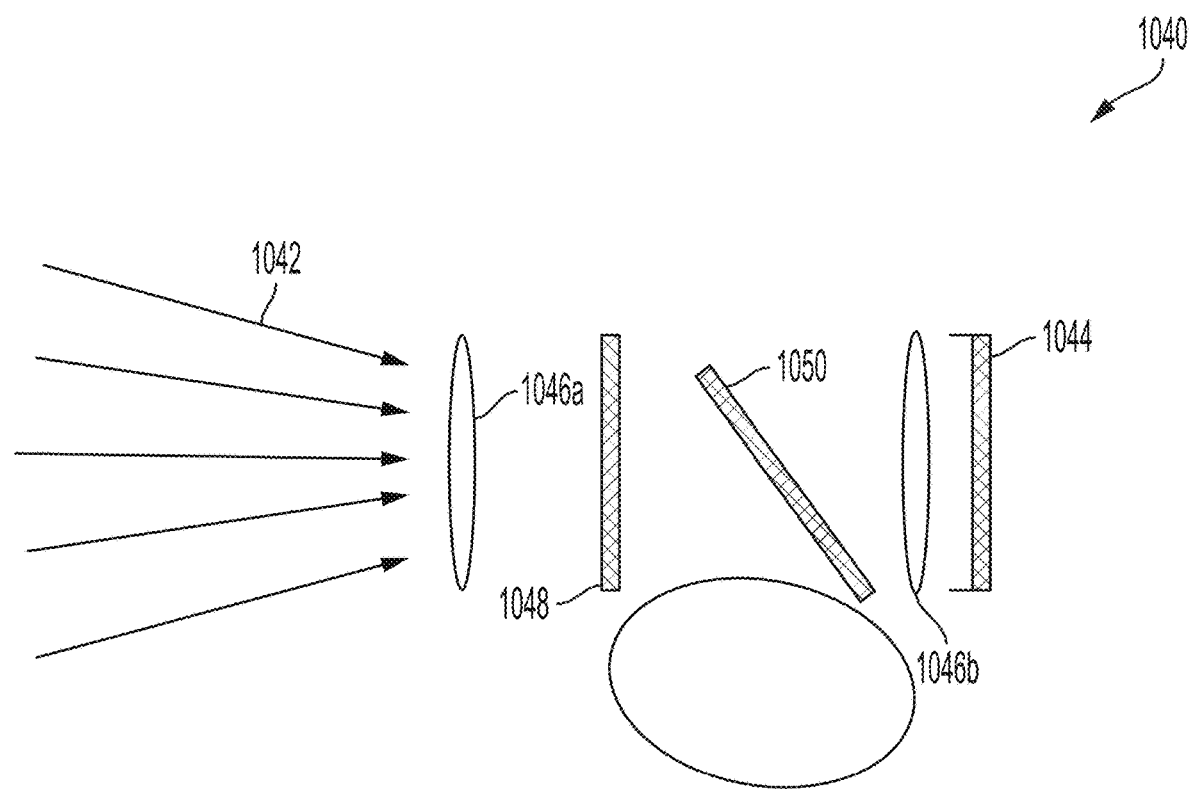
FIG. 12 is an exemplary camera module of a fluorescence imaging system, according to some embodiments.

Referring again to FIG. 10, in some variations, the image acquisition assembly 1016 may be a component of a fluorescence imaging system 1010 configured to acquire the time series and/or subject time series of fluorescence images from the fluorescence emission from the fluorescence imaging agent 1014. The image acquisition assembly 1016 may include a camera module 1040. As shown in FIG. 12, the camera module 1040 may acquire images of the fluorescence emission 1042 from the fluorescence imaging agent in the tissue by using a system of imaging optics (e.g., 1046a, 1046b, 1048 and 1050) to collect and focus the fluorescence emission onto an image sensor assembly 1044. The image sensor assembly 1044 may comprise at least one 2D solid state image sensor. The solid state image sensor may be a charge coupled device (CCD), a CMOS sensor, a CID or similar 2D sensor technology. The charge that results from the optical signal transduced by the image sensor assembly 1044 is converted to an electrical video signal, which includes both digital and analog video signals, by the appropriate read-out and amplification electronics in the camera module 1040.

According to an exemplary variation of a fluorescent imaging system, the light source may provide an excitation wavelength of about 800 nm+/−10 nm, and the image acquisition assembly uses emission wavelengths of >820 nm with NIR-compatible optics for, for example, ICG fluorescence imaging. In an exemplary embodiment, the NIR-compatible optics may include a CCD monochrome image sensor having a GigE standard interface and a lens that is compatible with the sensor with respect to optical format and mount format (e.g., C/CS mount).

In some variations, the processor module 1062 comprises any computer or computing means such as, for example, a tablet, laptop, desktop, networked computer, or dedicated standalone microprocessor. For instance, the processor module 1062 may include one or more central processing units (CPU). In an exemplary embodiment, the processor module 1062 is a quad-core, 2.5 GHz processor with four CPUs where each CPU is a microprocessor such as a 64-bit microprocessor (e.g., marketed as INTEL Core i3, i5, or i7, or in the AMD Core FX series). However, in other embodiments, the processor module 1062 may be any suitable processor with any suitable number of CPUs and/or other suitable clock speed.

Inputs for the processor module 1062 may be taken, for example, from the image sensor 1044 of the camera module 1040 shown in FIG. 12, from the solid state photodiode 1030 in the illumination module 1020 in FIG. 11, and/or from any external control hardware such as a footswitch or remote-control. Output is provided to the laser diode driver and optical alignment aids. As shown in FIG. 10, in some variations, the processor assembly 1018 may have a data storage module 1064 with the capability to save the time series/subject time series of images, or data representative thereof, or other input data to a tangible non-transitory computer readable medium such as, for example, internal memory (e.g. a hard disk or flash memory), so as to enable recording and processing of acquired data. In some variations, the processor module 1062 may have an internal clock to enable control of the various elements and ensure correct timing of illumination and sensor shutters. In some variations, the processor module 1062 may also provide user input and graphical display of outputs. The fluorescence imaging system may optionally be configured with a communication unit 1066, such as a wired or wireless network connection or video output connection for transmitting the time series of fluorescence images as they are being acquired or played back after recording. The communication unit 1066 may additionally or alternatively transmit processed data, such as a spatial map, a subject spatial map, and/or tissue numerical value.

In operation of the exemplary system described in FIGS. 10-12, the subject is positioned relative to fluorescence imaging system 1010 such that an area of interest (e.g., target tissue region) is located beneath the light source 1012 and the image acquisition assembly 1016 such that the illumination module 1020 of light source 1012 produces a substantially uniform field of illumination across substantially the entire area of interest. In some variations, prior to the administration of the fluorescence imaging agent 1014 to the subject, an image may be acquired of the area of interest for the purposes of background deduction. To acquire fluorescence images/subject fluorescence images, the operator of the fluorescence imaging system 1010 may initiate the acquisition of the time series/subject time series of fluorescence images by depressing a remote switch or foot-control, or via a keyboard (not shown) connected to the processor assembly 1018. As a result, the light source 1012 is turned on and the processor assembly 1018 begins recording the fluorescence image data/subject fluorescence image data provided by the image acquisition assembly 1016. When operating in the pulsed mode of the embodiment, the image sensor 1044 in the camera module 1040 is synchronized to collect fluorescence emission following the laser pulse produced by the diode laser 822 in the illumination module 1020. In this way, maximum fluorescence emission intensity is recorded, and signal-to-noise ratio is optimized. In this embodiment, the fluorescence imaging agent 1014 is administered to the subject and delivered to the area of interest via arterial flow. Acquisition of the time series/subject time series of fluorescence images is initiated, for example, shortly after administration of the fluorescence imaging agent 1014, and the time series of fluorescence images from substantially the entire area of interest is acquired throughout the ingress of the fluorescence imaging agent 1014. The fluorescence emission from the region of interest is collected by the collection optics of the camera module 1040. Residual ambient and reflected excitation light is attenuated by subsequent optical elements (e.g., optical element 1050 in FIG. 12 which may be a filter) in the camera module 1040 so that the fluorescence emission can be acquired by the image sensor assembly 1044 with minimal interference by light from other sources.

In some variations, following the acquisition or generation of the time series/subject time series of fluorescence images, the processor assembly 1018 (e.g., processor module 1062 or other processor) may then be initiated to execute instructions stored on memory 1068 and process the imaging data before transmission to the imaging data processing system (e.g., hub 102 of system 100). The system 1010 may transmit, via connection 1066, the spatial map/subject spatial map and/or any clinical correlations or diagnosis derived therefrom or both for display to the user in a composite display feed as, for example, a grayscale or false color image, and/or stored for subsequent use.

Figure 13:
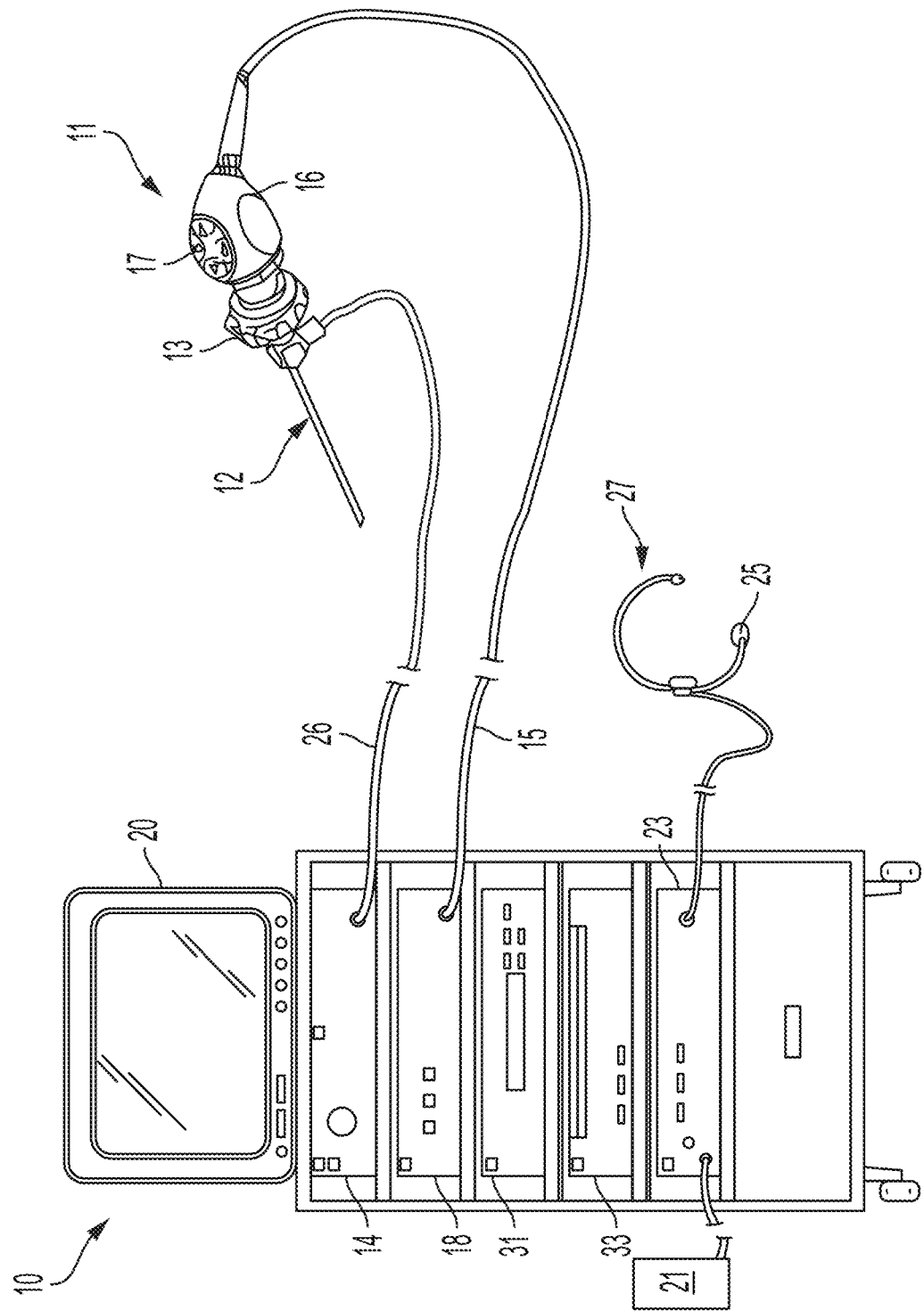
FIG. 13 is an exemplary endoscopic imaging cart, according to some embodiments.

FIG. 13 shows an endoscopic surgical cart embodiment of system 100 of FIG. 1. Cart 10 may be used, for example, in an operating room for endoscopic imaging and display during an endoscopic procedure. Cart 10 includes an imaging system, such as fluorescence imaging system 1010 of FIG. 10. The imaging system includes a scope assembly 11 which may be utilized in endoscopic procedures. The scope assembly 11 incorporates an endoscope or scope 12 which is coupled to a camera head 16 by a coupler 13 located at the distal end of the camera head 16. Light is provided to the scope by a light source 14 via a light guide 26, such as a fiber optic cable. The camera head 16 is coupled to a camera control unit (CCU) 18 by an electrical cable 15. The CCU 18 is preferably connected to, and communicates with, the light source 14. Operation of the camera 16 is controlled, in part, by the CCU 18. The cable 15 conveys video image data from the camera head 16 to the CCU 18 and conveys various control signals bi-directionally between the camera head 16 and the CCU 18. In one embodiment, the image data output by the camera head 16 is digital.

A control or switch arrangement 17 is provided on the camera head 16 and allows a user to manually control various functions of the cart 10. Voice commands may be input into a microphone 25 mounted on a headset 27 worn by a surgeon and coupled to a voice-control unit 23. Cart 10 may include a hand-held control device 21, such as a tablet with a touch screen user interface or a PDA, that may be coupled to the cart 10 as a further control interface. The cart 10 also includes an imaging data processing hub 31, such as hub 102 of FIG. 1 or hub 400 of FIG. 4, which is coupled to the imaging system via one or more cable connections for receiving images and/or video from the imaging system, processing the images and/or video, and generating display feeds for display on display 20 according to the methods described herein. The imaging data processing hub may receive user input via the voice control unit and/or through the hand-held control device.

Cart 10 may include one or more additional devices 33, such as an imaging recording device or a surgical tool control device, which may be coupled to the imaging data processing hub. The imaging data processing hub 31 may receive information from the one or more additional devices 33, such as device warnings, device status, and device settings. In some embodiments, the additional device 33 is a video recorder, and the imaging data processing hub 31 may transmit one or more display feeds to the video recorder for recording.

A tangible non-transitory computer readable medium having computer-executable (readable) program code embedded thereon may provide instructions for causing one or more processors to, when executing the instructions, perform one or more of the methods described herein. Program code can be written in any appropriate programming language and delivered to the processor in many forms, including, for example, but not limited to information permanently stored on non-writeable storage media (e.g., read-only memory devices such as ROMs, CD-ROM disks, etc.), information alterably stored on writeable storage media (e.g., hard drives or the like), information conveyed to the processor through communication media, such as a local area network, a public network such as the Internet, or any type of media suitable for storing electronic instruction. When carrying computer readable instructions that implement the various embodiments of the methods described herein, such computer readable media represent examples of various embodiments. In various embodiments, the tangible non-transitory computer readable medium comprises all computer-readable media, and the present invention scope is limited to computer readable media wherein the media is both tangible and non-transitory.

A kit may include any part of the systems described herein and the fluorescence imaging agent such as, for example, a fluorescence dye such as ICG or any suitable fluorescence imaging agent. In further aspects, a kit may include a tangible non-transitory computer readable medium having computer-executable (readable) program code embedded thereon that may provide instructions for causing one or more processors, when executing the instructions, to perform one or more of the methods for characterizing tissue and/or predicting clinical data described herein. The kit may include instructions for use of at least some of its components (e.g., for using the fluorescence imaging agent, for installing the computer-executable (readable) program code with instructions embedded thereon, etc.). In yet further aspects, there is provided a fluorescence imaging agent such as, for example, a fluorescence dye for use in in the methods and systems described herein. In further variations, a kit may include any part of or the entire system described herein and a fluorescence agent such as, for example, a fluorescence dye such as ICG, or any other suitable fluorescence agent, or a combination of fluorescence agents.

Example Imaging Agents for Use in Generating Imaging Data

According to some embodiments, in fluorescence medical imaging applications, the imaging agent is a fluorescence imaging agent such as, for example, ICG dye. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 µM to about 10 µM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. A fluorescence dye includes any non-toxic fluorescence dye. In certain embodiments, the fluorescence dye optimally emits fluorescence in the near-infrared spectrum. In certain embodiments, the fluorescence dye is or comprises a tricarbocyanine dye. In certain embodiments, the fluorescence dye is or comprises ICG, methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality. Such fluorescence agents may be administered into body fluid (e.g., lymph fluid, spinal fluid) or body tissue.

In some variations, the fluorescence imaging agent used in combination with the methods, systems and kits described herein may be used for blood flow imaging, tissue perfusion imaging, lymphatic imaging, or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

In variations relating to cardiac applications, the imaging agent(s) (e.g., ICG alone or in combination with another imaging agent) may be injected intravenously through, for example, the central venous line, bypass pump and/or cardioplegia line to flow and/or perfuse the coronary vasculature, microvasculature and/or grafts. ICG may be administered as a dilute ICG/blood/saline solution down the grafted vessel such that the final concentration of ICG in the coronary artery is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes require involvement of a nuclear physician and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticarial and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various embodiments for use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue (for comparison). One 25 mg vial of ICG may be reconstituted with 10 ml sterile water for injection to yield a 2.5 mg/ml solution immediately prior to ICG administration. Using a TB syringe and a 30G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast. ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to highlight/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages: high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, florescence is easier to detect intra-operatively than blue staining (isosulfan blue) of lymph nodes. In other variations, the methods, dosages or a combination thereof as described herein in connection with lymphatic imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement. In some embodiments, blood flow and tissue perfusion imaging described herein in connection with the systems and methods may be used to image tumor tissue and differentiate such tissue from other tissue.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for displaying medical imaging data comprising:
   receiving first image data generated by a first medical imaging device, wherein the first image data comprises a field of view (FOV) portion and a non-FOV portion, wherein the non-FOV portion is a portion of the imaging data that does not correspond to any portion of a scene;
   analyzing the first image data to identify the non-FOV portion of the first image data;
   generating cropped first image data by removing at least a portion of the non-FOV portion of the first image data that was identified based on the analysis of the first image data; and
   displaying the cropped first image data in a first portion of a display and additional information in a second portion of the display.

2. The method of claim 1, wherein the non-FOV portion is identified using edge detection.

3. The method of claim 2, wherein the first image data comprises a series of video frames and the edge detection is performed on more than one frame.

4. The method of claim 1, wherein the non-FOV portion is identified using one or more of a location of a center of the FOV portion and a measurement associated with a dimension of the FOV portion.

5. The method of claim 4, wherein the location of a center of the FOV portion and the measurement associated with a dimension of the FOV portion are determined during an imaging session initialization process.

6. The method of claim 5, wherein the imaging session initialization process is a white balancing process.

7. The method of claim 1, wherein the first image data comprises a rectangular image or video frame and the FOV portion is a circular portion of the rectangular image or video frame.

8. The method of claim 1, wherein the first image data comprises a video frame.

9. The method of claim 1, wherein the first image data is received on a first input of a medical imaging processing system and the additional information is based on data received on a second input of the medical imaging processing system.

10. The method of claim 9, comprising transmitting a display feed from the medical imaging processing system to the display, the display feed comprising a combination of the cropped first image data and the additional information.

11. The method of claim 1, further comprising:
    receiving second image data generated by a second medical imaging device;
    identifying a non-FOV portion of the second image data;
    generating cropped second image data by removing at least a portion of the non-FOV portion of the second image data; and
    displaying the cropped second image data in the second portion of the display.

12. The method of claim 11, wherein the first image data is received on a first input of a medical imaging processing system and the second image data is received on a second input of the medical imaging processing system.

13. The method of claim 12, comprising transmitting a display feed from the medical imaging processing system to the display, the display feed comprising a combination of the cropped first image data and the cropped second image data.

14. The method of claim 1, wherein the cropped first image data and the additional information are located on the display based on configuration data stored in a memory.

15. The method of claim 14, wherein the configuration data comprises user-specified configuration data.

16. The method of claim 15, wherein the configuration data is received via a network connection.

17. The method of claim 1, wherein the first image data is received from an endoscopic imaging system, an intraoperative C-arm imaging system, or an ultrasound system.

18. The method of claim 17, wherein the first image data is received from a camera control unit.

19. The method of claim 1, wherein the additional information comprises one or more of patient data, metrics, a graph, an image, device status, and a video feed.

20. A system for displaying medical imaging data comprising:
   one or more data inputs;
   one or more processors; and
   one or more displays,
   wherein the one or more data inputs are configured for receiving first image data generated by a first medical imaging device, wherein the first image data comprises a field of view (FOV) portion and a non-FOV portion, wherein the non-FOV portion is a portion of the imaging data that does not correspond to any portion of a scene, and
   the one or more processors are configured for analyzing the first image data to identify the non-FOV portion of the first image data and generating cropped first image data by removing at least a portion of the non-FOV portion of the first image data that was identified based on the analysis of the first image data, and transmitting the cropped first image data for display in a first portion of the one or more displays and additional information for display in a second portion of the one or more displays.

21. The system of claim 20, wherein the one or more processors are configured to identify the non-FOV portion using edge detection.

22. The system of claim 21, wherein the one or more processors are configured to perform edge detection on more than one frame of a series of video frames.

23. The system of claim 20, wherein the one or more processors are configured to identify the non-FOV portion using one or more of a location of a center of the FOV portion and a measurement associated with a dimension of the FOV portion.

24. The system of claim 23, wherein the location of a center of the FOV portion and the measurement associated with a dimension of the FOV portion are determined during an imaging session initialization process.

25. The system of claim 24, wherein the imaging session initialization process is a white balancing process.

26. The system of claim 20, wherein the first image data comprises a rectangular image or video frame and the FOV portion is a circular portion of the rectangular image or video frame.

27. The system of claim 20, wherein the first image data comprises a video frame.

28. The system of claim 20, wherein the first image data is received on a first input of the one or more data inputs and the additional information is based on data received on a second input of the one or more data inputs.

29. The system of claim 20, wherein the one or more processors are configured for:
   receiving second image data generated by a second medical imaging device;
   identifying a non-FOV portion of the second image data;
   generating cropped second image data by removing at least a portion of the non-FOV portion of the second image data; and
   transmitting the cropped second image data for display in the second portion of the display.

30. The system of claim 29, wherein the first image data is received on a first input of the one or more data inputs and the second image data is received on a second input of the one or more data inputs.

31. The system of claim 20, wherein an arrangement of the cropped first image data and the additional information for display is based on configuration data stored in a memory of the system.

32. The system of claim 31, wherein the configuration data comprises user-specified configuration data.

33. The system of claim 32, wherein the configuration data is received via a network connection.

34. The system of claim 20, wherein the system is configured to receive the first image data from an endoscopic imaging system, an intraoperative C-arm imaging system, or an ultrasound system.

35. The system of claim 34, wherein the system is configured to receive the first image data from a camera control unit.

36. The system of claim 20, wherein the additional information comprises one or more of patient data, metrics, a graph, an image, device status, and a video feed.

* * * * *